United States Patent [19]
Bonewald et al.

[11] Patent Number: 5,534,524
[45] Date of Patent: Jul. 9, 1996

[54] SUPPRESSION OF BONE RESORPTION BY QUINOLINES

[75] Inventors: Lynda Bonewald; G. R. Mundy; Wolf E. Gallwitz, all of San Antonio, Tex.

[73] Assignee: Board of Regents, The University of Texas System, Austin, Tex.

[21] Appl. No.: 240,027

[22] Filed: May 9, 1994

[51] Int. Cl.⁶ .................. A61K 31/47; A61K 31/505; A61K 31/44; A61K 31/35
[52] U.S. Cl. .................. 514/314; 514/259; 514/311; 514/307; 514/302; 514/451; 514/453; 514/460
[58] Field of Search .................... 514/259, 311, 514/302, 314, 451, 453, 460, 307, 418

[56] References Cited

PUBLICATIONS

Agarwal et al., "Nordihydroguaiaretic Acid, an Inhibition of Lipoxygenase, also Inhibits Cytochrome P–450–Medicate Monooxygenase Activity in Rat Epidermal and Hepatic Microsome," *Drug Metabolism and Disposition*, 19(3): 620–623, 1991.

Crawley et al., "Methoxytetrahydropyrans. A New Series of Selective and Orally Potent 5–Lipoxygenase Inhibitors," *J. Med. Chem.*, 35:2600–2609, 1992.

Gallwitz et al., "5–Lipoxygenase Metabolites of Arachidonic Acid Stimulate Isolated Osteoclasts to Resorb Calcified Matrices," *The Journal of Biological Chemistry*, 268(14):10087–10094, 1993.

Huang et al., "Differential Effects of a Series of Hydroxamic Acid Derivatives on 5–Lipoxygenase and Cyclooxygenase from Neutrophils and 12–Lipoxygenase from Platelets and Their In Vivo Effects on Inflammation and Anaphylaxis," *J. Med. Chem.*, 32:1836–1842, 1989.

Gillard et al., "L–663, 536 (MK–886) (3–[1–(4–chlorobenzyl)–3–butylthio–5–isoproylindol–2–yl] –2,2–dimethylpropanoic acid), a novel, orally active leukotriene biosynthesis inhibitor," *Can. J. Physiol. Pharmacol.*, 67:456–464, 1989.

McMillan et al., "Pre–clinical Pharmacology of ICI D2138, a Potent Orally–Active Non–Redox Inhibitor of 5–Lipoxygenase," *Br. J. Pharmacol.*, 107:1042–1047, 1992.

Oreffo et al., "Inhibitory Effects of the Bone–Derived Growth Factors Osteoinductive Factor and Transforming Growth Factor–β on Isolated Osteoclasts," *Endocrinlogy*, 126(6):3069–3075, 1990.

Oreffo et al., "Characterization of a Cell Line Derived From a Human Giant Cell Tumor that Stimulates Osteoclastic Bone Resorption," *Clinical Orthopaedics and Related Research*, 296:229–241, 1993.

Mundy, "Cytokines and growth factors in the regulation of bone remodeling," *J. Bone Miner. Res.*, 8/Suppl.2:S505–S510, 1993.

Sietsema et al., "Absorption, Bioavailability, and Pharmacokinetics of Tebufelone in the Rat," *Journal of Pharmaceutical Sciences*, 82, 6:610–612, 1993.

Wiesenberg–Boettcher et al., "The Pharmacological Profile of CGP 28238, A Novel Highly Potent Anti–Inflammatory Compound," *Drugs Exptl. Clin. Res.*, 15 11/12:501–509, 1989.

*Primary Examiner*—Theodore J. Criares
*Attorney, Agent, or Firm*—Arnold White & Durkee

[57] ABSTRACT

The present invention focuses upon a method for inhibiting bone resorption. This method involves administering a 5-lipoxygenase inhibitor to a subject in an amount inhibiting the effects of an osteoclast-stimulating factor. When the production of the osteoclast-stimulating factors such as PTH, PTHrp, IL-1, TNF, LT, 1,25(OH)$_2$D$_3$ or other factors which may stimulate the production of 5-LO metabolites via the 5-lipoxygenase pathway is inhibited, bone resorption markedly declines. The direct osteoclast-stimulating factors include leukotriene, peptidoleukotriene and 5-hydroxyeicosatetraenoic acid. Other factors yet to be identified or previously known may also be 5-lipoxygenase metabolites that stimulate bone resorption. While 5-lipoxygenase inhibitors may be substrate analogs or allosteric inhibitors, a substance which inhibits the activity of this enzyme may utilize other mechanisms (e.g., inhibition of 5-LO biosynthesis) and nevertheless function to inhibit bone resorption. Preferred inhibitors included NGDA, MK886 and ZM230, 487. The best inhibitor thus far noted is ZM230,487. The inhibition of bone resorption is highly desirable with, for example, periodontal disease, osteoporosis, estrogen deficiency, Paget's disease, inflammatory bone loss, bone malignancy, hyperparathyroidism. The preferred range of 5-lipoxygenase inhibitors administered is from 0.1 to 10 mg/kg body weight/day.

11 Claims, 21 Drawing Sheets

AR = 1 Me-quinol-2-on-6-yl
R$^1$ = 5F
R$^2$ = Et
n = 2
m = 2
Z = 0

SUPPRESSION OF BONE RESORPTION BY QUINOLINES

The United States government has rights in the present invention because relevant research was supported by Grant NIH-POI AR 39529.

BACKGROUND OF THE INVENTION

Diseases associated with bone loss are usually accompanied by increased osteoclast activation. Such diseases include estrogen deficiency after the menopause, osteoporosis, primary hyperparathyroidism, malignancy, Paget's disease of bone and periodontal disease. The bone loss is caused by osteoclast activity. Osteoclasts are unique multinucleated cells within bone that are responsible for bone degradation. These are the only cells in the body known to be capable of resorbing bone. Since diseases of bone loss are associated with increased activity of these cells, it is important to understand the mechanisms by which osteoclasts are activated in these disease states, and to devise rational and therapeutic means to inhibit this activation.

The molecular mechanisms by which osteoclasts are activated are unknown. In vitro data indicate cytokines and systemic hormones with bone resorbing effects do not act directly on osteoclasts, but rather act on accessory cells in the bone marrow microenvironment and that these cells in turn are responsible for osteoclast activation (Rodan & Martin 1981, McSheehy & Chambers 1986). This activation may be mediated either by cell-cell contact or by locally active soluble factors. In a search for cell sources of such soluble factors, the present inventors found that a stromal cell line (C433) derived from a giant cell tumor of bone produced prodigious amounts of osteoclast-stimulating activity greater than any we found in conditioned media from cells with osteoblast characteristics (Oreffo et al., 1993).

Human giant cell tumors of bone comprise heterogeneous cell populations, including giant cells with many of the phenotypic and functional characteristics of osteoclasts as well as mononuclear cells. The multinucleated cells are positive for osteoclast surface antigens (Davies et al, 1989), for tartrate-resistant acid phosphatase (TRAP),[1] possess receptors for calcitonin (Komiya et al., 1990) and lack monocyte-macrophage surface antigens (Goldring et al., 1986). The mononuclear cells comprise two distinct populations. One population does not persist in culture and is positive for Ia and monocyte-macrophage antigens (Ling et al., 1988). Another population persists in culture and resembles connective tissue stromal cells, produces Types I and III collagen, and has receptors for parathyroid hormone (Goldring et al., 1986). These latter cells can be readily established in cell culture. One cell line (C433) derived from stomal cells from a giant cell tumor is shown herein to cause greater increases in osteoclast activity as measured by accumulation of TRAP activity than any of the known osteoblast-like cell lines. This study concerns characterizing the osteoclast stimulating activity produced by this cell line. This activity is ascribed to 5-hydroxyeicosanoids, which are 5-lipoxygenase metabolites of arachidonic acid.

[1] The abbreviations used include: TRAP, tartrate-resistant acid phosphatase; HETE, hydroxyeicosatetraenoic acid; HPLC, high pressure measure liquid chromatography; $LTC_4$, $LTD_4$, and $LTE_4$, leukotriene $C_4$, leukotriene $D_4$, and leukotriene $E_4$; GC-MS, gas chromatography-mass spectrometry, 5-LO, 5-lipoxygenase.

Dziak and co-workers (Mohammed et al., 1989) examined the role of leukotrienes in orthodontic tooth movement, a model used to examine bone remodeling. These investigators found significant inhibition of tooth movement using the leukotriene inhibitor AA 861, even though enhanced levels of prostaglandins were detected in this treated tissue. They suggested that inhibition of LT synthesis might influence tooth movement and that prostaglandins and leukotrienes might mediate different steps in a cascade of events that results in initiation of bone remodeling.

5-lipoxygenase metabolites possess a diverse range of biological activities, especially in allergic and inflammatory responses. The molecule LTB-4 is chemotactic for polymorphonuclear leukocytes, eosinophils, lymphocytes, and monocytes and will increase adherence, oxygen radical production, and lysosomal degranulation in polymorphonuclear leukocytes (Goldman et al., 1986). LTC-4 and LTD-4 have been shown to promote myeloid colony formation (Ziboh et al., 1986), proliferation of glomerular epithelial cells (Baud et al., 1985), and secretion of luteinizing hormone and luteinizing hormone releasing-hormone (Parker 1987). A number of cytokines and growth factors such as interleukin-1 and interleukin-2 will induce production and secretion of leukotrienes (Parker 1987). Significant breakthroughs have been made in identifying proteins and enzymes involved in the synthesis of these compounds. For example, only cells which contain both 5-lipoxygenase (5-LO) and a recently cloned protein, 5-lipoxygenase-activating protein (FLAP), will produce leukotrienes (Dixon et al., 1990; Reid et al., 1990). Hormones which induce 5-LO metabolite production may regulate not only 5-LO enzymes but FLAP expression.

There are previous reports that leukotrienes (LT) may be modulators of bone cell function. Meghji et al (1988) tested purified leukotrienes in the neonatal mouse calvarial assay and found significant bone resorption. However, other investigators have not been able to repeat these results (personal communications). This may be due to the unstable nature of these compounds. The present inventors now report that special precautions are necessary to maintain biological activity. The compounds must be stored under argon in the absence of light. Once removed from these conditions the commercial compounds must be diluted quickly and used immediately. Activity of commercially available compounds was detectable at higher concentrations ($10^{-6}$ to $10^{-7}$M) in the organ culture assay, whereas activity was detectable at much lower concentrations ($10^{-10}$ to $10^{-11}$M) in the isolated avian osteoclast and isolated human giant cell assays. This may reflect readier access of 5-LO metabolites to target cells in the isolated cell culture system.

Thus, the mechanisms by which leukotrienes and other systemic factors and hormones are responsible for osteoclast activation remain unknown. The connection between leukotrienes and other systemic hormones and bone resorbing factors and whether their effects on osteoclasts are related or independent was also unknown prior to the information described by the present application.

Inhibitors of 5-Lipoxygenase used herein include:
NGDA—nordihydroguaiaretic acid (see structure in FIG. 9);
MK886—(see structure in FIG. 10); and
ZM230,487—(see structure in FIG. 11)

SUMMARY OF THE INVENTION

The present invention focuses upon a method for inhibiting bone resorption. This method involves administering a 5-lipoxygenase inhibitor to a subject in an amount suppressing production of an osteoclast-stimulating factor. When the production of the osteoclast-stimulating factors via the 5-lipoxygenase pathway is inhibited, bone resorption markedly declines. The osteoclast-stimulating factors include peptido-leukotriene and 5-hydroxyeicosatetraenoic acid. Other factors yet to be identified or previously known may also be 5-lipoxygenase metabolites that stimulate bone resorption. While 5-lipoxygenase inhibitors may be substrate analogs or allosteric inhibitors, a substance which inhibits the activity of this enzyme may utilize other mechanisms (e.g., inhibition of 5-LO biosynthesis) and nevertheless function to inhibit bone resorption. Preferred inhibitors included NGDA, MK886 and ZM230,487. The best inhibitor thus far noted is ZM230,487.

The inhibition of bone resorption is highly desirable with, for example, periodontal disease, osteoporosis, estrogen deficiency, Paget's disease, inflammatory bone loss, bone malignancy, hyperparathyroidism. Administering of a 5-lipoxygenase inhibitor may be enteral—when oral administration is desired, parenteral, when appropriate (preferably by vascular injection or infusion), or topical such as application to oral tissues to prevent bone loss due to periodontal disease. The preferred range of 5-lipoxygenase inhibitors administered is from 0.1 to 10 mg/kg body weight/day.

BRIEF DESCRIPTION OF THE DRAWINGS

FIG. 3A. C433-conditioned medium was treated with ultraviolet light (UV) for 24 h or placed in a boiling water bath (100° C.) for 15 min and bioassayed. FIG. 3B. amino peptidase M (A), carboxypeptidase (C), or Pronase-CB (P) were incubated in the presence of C433-conditioned medium for 12 h at 37° C. FIG. 3C. 433 cells treated with flurbiprofen (FLUR), $10^{-6}$M indomethacin (INDO) $10^{-6}$M, or $10^{-5}$M nordihydroguaiaretic acid (NDGA). The resultant conditioned medium was bioassayed for activity. FIG. 3D. C433 were treated with $10^{-6}$, $10^{-5}$ or $10^{-4}$M nordihydroguaiaretic acid. Conditioned medium was bioassayed for induction of TRAP activity in avian osteoclasts.

FIG. 4A. Commercially available (Sigma) LTC$_4$/LTD$_4$ (1.2 µg) and 5-HETE (5 µg) were applied to a C$_8$ reverse phase HPLC under the exact conditions as C433-conditioned medium. FIG. 4B. LTC$_4$/LTD$_4$ standard eluted at the same fraction as activity 2 whereas FIG. 4C 5-HETE standard (85% methanol) eluted as activity 3. MUP, methylumbelliferyl phosphate.

FIG. 13(A) shows the number of resorption lacunae per osteoclast. FIG. 13(B) shows the area of resorption lacunae per osteoclast.

DETAILED DESCRIPTION OF THE PREFERRED EMBODIMENTS

Figure 1A:
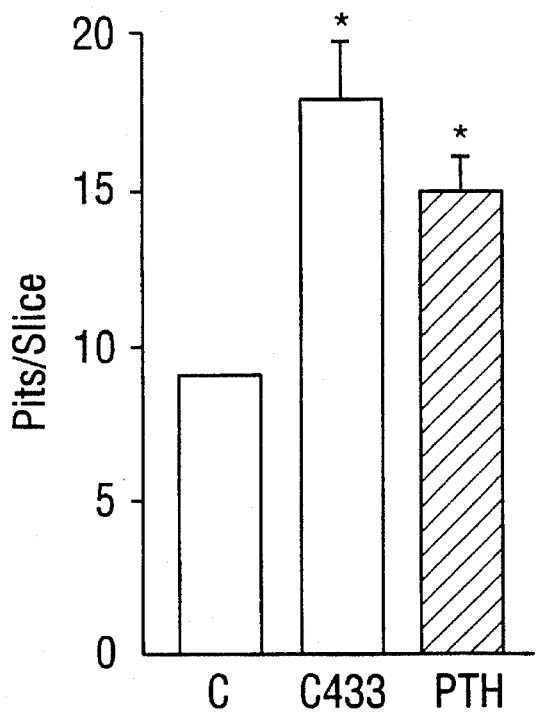
FIGS. 1A–1D. Quantitation of pit formation on sperm whale dentine by rat osteoclasts treated with C433-conditioned medium (DMEM, 0.1% BSA, $10^{-8}$M 1,25-(OH)$_2$ vitamin D$_3$), with parathyroid hormone (PTH) ($10^{-8}$M) and C=control (DMEM, 0.1% BSA, $10^{-8}$M 1,25-(OH)$_2$ vitamin D$_3$) (FIG. 1A) or human giant cells treated with C433-conditioned medium (FIG. 1B). Quantitation of TRAP activity by avian osteoclasts incubated with C433-conditioned medium (FIG. 1C) and human giant cells incubated with C433-conditioned medium (FIG. 1D). T/C=treated/control ratio.

The present invention comprises (1), a method for treating osteoporosis by inhibition of osteoclastic bone resorption, (2), a method for treating Paget's disease of bone by inhibition of osteoclastic bone resorption, (3), a method for treating metastatic cancer in bone by inhibition of bone resorption, (4), a method of treating periodontal disease by inhibition of bone resorption, and (5), a method for treating other diseases associated with increased osteoclastic bone resorption. Bone resorption may be inhibited by inhibitors to show the production of metabolites stimulating osteoclasts. While a number of 5LO inhibitors are described herein, it is understood that many others are possible. The assays for such inhibitors described herein enable others to be readily developed.

For each of these diseases, 5-lipoxygenase inhibitors may be enterally or parenterally administered. The doses, duration of treatment and timing of administration would need to be determined by Phase I clinical studies, but based on in vitro data should be in the range of 0.1–10 mg/kg/day. The compound could also be applied topically such as creams or toothpaste for periodontal disease.

Bone resorption requires cooperation between osteoclasts and mononuclear accessory cells by mechanisms which have not been elucidated. Multinucleated cells in giant cell tumors of bone have many phenotypic and functional characteristics of normal osteoclasts. The interaction between the bone-resorbing multinucleated cells and the distinct mononuclear stromal cells from these tumors was examined. These mononuclear cells produce an activity which stimulates both giant cells from giant cell tumors and rodent osteoclasts to resorb bone in vitro. The activity has been identified and found that it represents several products of the 5-lipoxygenases pathway of arachidonic acid metabolism, for example, 5-hydroxyeicosatetraenoic acid and the leukotrienes. As described herein, 5-lipoxygenase metabolites stimulate isolated osteoclasts to resorb bone in vitro and represent a mechanism by which mononuclear stromal cells in human giant cell tumors communicate with the giant cells. In addition, the results desorbed herein explain one mechanism for communication between accessory cells and osteoclasts involved in normal bone resorption.

The present inventors show that leukotriene compounds, in addition to other systemic hormones such as parathyroid hormone and 1,25 dihydroxyvitamin $D_3$ and cytokines such as interleukin-1 and tumor necrosis factor, are capable of inducing bone resorption both in vitro and in vivo (Gallwitz et al, 1993). This was shown by studies on the cells isolated from human giant cell tumors of bone. The giant cells and giant cell tumors of bone resemble osteoclasts, but other cells in these tumors produce factors which activate the osteoclasts. These factors have been identified and it was found that they represent several products of the 5 lipoxygenase pathway of arachidonic acid metabolism, the leukotrienes. The data indicate that these 5 lipoxygenase metabolites stimulate isolated osteoclasts to resorb bone in vitro.

The following examples illustrate the best mode and technical background of the present invention. They should not limit the claims of the present invention unless otherwise specified.

EXAMPLE 1

5-Lipoxygenase Metabolites of Arachidonic Acid Stimulate Isolated Osteoclasts to Resorb Calcified Matrices

EXPERIMENTAL PROCEDURES

Materials

The radioimmunoassays for 5-HETE were purchased from Advanced Magnetics, Inc. (Cambridge, Mass.). The commercially available 5-HETE and leukotrienes, protease enzymes, flurbiprofen, indomethacin, and nordihydroguaiaretic acid were purchased from Sigma.

Isolation of Avian Osteoclasts

Avian osteoclasts were isolated from medullary bone of laying White Leghorn hens *Gallus domesticus* (Pioneer Animal Supply, Kingswheel, Ohio) as described previously by Zambonin-Zallone and Teti (1981). In brief, bone marrow suspensions from the medullary bone of femora were filtered through Nytex cloth (110 μm, t'etko, Elmsford, N.Y.), centrifuged for 5 min at 1200 rpm, and the cell pellet resuspended in 0.2% NaCl for 3 min to lyse erythrocytes. After layering the cells on 100% fetal bovine serum for 1 h, sedimented cells were further filtered through Nytex filters (55 μm). Cells were harvested, resuspended in α-minimal Eagle's medium (GIBCO) containing 10 fetal bovine serum, with penicillin (100 units/ml), streptomycin (100 μg/ml), and Ara-C, to inhibit proliferation of nonosteoclastic cells. Cells were plated in 24- or 48-well plates (Costar, Cambridge, Mass.) at $1 \times 10^4$ cells/well and incubated at 37° C. in 10% $CO_2$ humidified air for 48 h, after which they were washed to remove nonadherent cells. When matured osteoclasts were observed experiments were begun and terminated within 48 h.

Quantitation of Tartrate-resistant Acid Phosphatase by Fluorescence Spectroscopy Osteoclast TRAP activity was measured using fluorescence spectroscopy as described by Chambers et al. (1987) with minor modifications. In brief, media from osteoclast cultures were harvested and stored at −70° C. until ready for assay.

The cells were washed with phosphate-buffered saline and harvested in 0.5 ml of Triton X-100 (0.05%, w/v). Aliquots of media or lysate 30 μl) were incubated with 170 μl of 2 mM methylumbelliferyl phosphate, pH 5.0, in 0.48M acetate buffer (0.48M sodium acetate, 0.48M acetic acid, pH 5.0) and 30 mM tartaric acid. Samples were incubated for 30 min at 37° C. and the reaction terminated with 100 μl of stop solution containing 50 mM glycine, 50 mM EDTA, pH 10.4. Fluorescence was measured at excitation 360 nm and emission 448 nm using a fluorimeter (Fluoroskan, Flow Instruments). Enzyme activity was expressed as micromoles of methylumbelliferyl phosphate hydrolyzed/min/μg of protein and the protein content measured by the technique of Lowry et al. (1951).

Disaggregated Neonatal Rat Osteoclast Pit Formation Assay

Quantitation of the effects of isolated osteoclasts on calcified matrices was determined using minor modifications of the disaggregated osteoclast resorption assay as described by Boyde et al. (1984). Sperm whale dentine (0.25×7×7 mm) was prepared using a Buehler low speed diamond saw (Buehler, Lake Bluff, Ill.) followed by sonication (15 min) in several changes of distilled water. Slices were sterilized using ultraviolet light.

Neonatal Sprague-Dawley rats (2–3 days) were sacrificed by decapitation, the femurs and tibias were removed, scraped free of adherent tissue, and trimmed free of the epiphyses. The bones from one litter were combined and quickly minced using a scalpel blade in 2 ml of 199 medium and then vigorously mixed with a pipette in an 8-ml tube, allowed to settle for 10 s, and then 100 µl of the suspension was added to each well for a total of 16 wells in a 48-well microtiter plate containing sperm whale dentine (approximately four neonates are used per 16 wells). The cells were incubated at 37° C. for 30 min at which time the dentine was removed, washed in media, and placed in a fresh 48-well plate containing 250 µl of test medium.

Osteoclasts were stained for TRAP and counted and then pit numbers were counted following toluidine blue (0.1% w/v) staining by light microscopy. The plan area of matrix resorbed was quantitated using a computer-assisted morphometric program on a Bioquant System IV analysis system (R & M Biometrics, Nashville, Tenn.).

Preparation of 23C6 Positive Cells from Giant Cell Tumors

Human giant cell tumors (normally discarded after surgery) were minced and passed through 1#40SS wire mesh screen, allowed to settle for 5 min, and the cell suspension above the sediment collected. The cells were incubated with 23C6 monoclonal antibody that identifies the osteoclast vitronectin receptor (generously provided by Dr. Michael Horton) (1:10 dilution of hybridoma supernatant/$10^6$ cells) at 4° C. in serum-free medium for 30 min, after which immunomagnetic beads coated with anti-mouse IgG (Dynabead, Dynal, Inc., Great Neck, N.Y.) were added to the cell suspension. The cell suspension was mixed for 5 min and then the 23C6 positive cells were separated using a magnet (Dynal, Inc.) on the side of the tube while suction was applied to remove all negative cells. Over 90% of the cells adhering to the magnetic beads were 23C6-positive, and these cells were used for induction of TRAP activity and for pit formation on sperm whale dentine. Cells were plated at 60 cells/dentine slice or $4 \times 10^4$ cells/well in 24-well plates for induction of TRAP activity.

Neonatal Mouse Calvarial Assay

The assay was performed as described by Gowen et al. (1983). Timed pregnant mice were injected with $^{45}Ca$ 2 days before parturition. Half-calvaria were removed from the 1–2-day-old pups and preincubated for 24 h in BGJb medium at 37° C. in a humidified atmosphere of 5% $CO_2$ before transfer to fresh media with or without test substances for 48 h. The bones were incubated for a further 72 h and media and bones collected. Bone-resorbing activity was expressed as the percentage of the total $^{45}Ca$ released into the medium.

Purification Protocol for the C433 Active Fractions

C433 cells were grown in 10% fetal bovine serum (Whittaker, Walkersville, Md.) 50% RPMI, 50% McCoys (Flow, McLean, Va.) until a density of $10^4$ cells/ml was obtained, at which time the cells were harvested, washed, and placed in serum-free DMEM plus $10^{-8}$ M, 1,25-$(OH)_2D_3$ for 48 h before harvest of conditioned medium. The conditioned medium was brought up to 15% ethanol and acidified to pH 3.5 with concentrated HCl. This conditioned medium was applied to a prewetted $C_{18}$ Sep-Pak (Millipore, Waters, Milford, Mass.), and bound material was extracted using ethyl acetate. This material was dried under nitrogen and resuspended in water, 1% acetic acid and analyzed by high pressure measure liquid chromatography (HPLC) (Waters, Milford, Mass.) applied to a $C_8$ semipreparative 25 cm×10 mm reverse phase column (Keystone Scientific, Inc., Bellefonte, Pa.) at 2 ml/min. The gradient was 0–100% methanol, 1% acetic acid over 60 min with 6-ml fractions collected. The fractions were dried under nitrogen, and those fractions to be assayed for osteoclast stimulating activity were stabilized with 20 µl of 10% bovine serum albumin. Fractions to be used for gas chromatography-mass spectrometric analysis were prepared for derivatization.

Gas Chromatography-mass Spectrometric Analysis for 5-Lipoxygenase Products

Bioactive HPLC fractions were analyzed for the presence of 5-lipoxygenase products using a modification of the procedure described by Balazy and Murphy (1986). Each fraction was supplemented with [8,9,20,11-$^{13}C_4$]$LTC_4$ (Raftery et al., 1992) and hydrogenated using a rhodium black catalyst. This procedure yields a common product, 5-hydroxyeicosanoic acid, from 5-lipoxygenase products such as 5-HETE and the peptido-leukotrienes. Each hydrogenated sample was converted to the pentafluorbenzyl ester trimethylsilyl ether derivative. Gas chromatographic-mass spectrometric analyses were performed with selected ion monitoring of ions characteristic of derivative of 5-hydroxyeicosanoic acid and of the [$^{13}C_4$] analogue.

Statistical Analysis

Data were analyzed using the Student's t test or the Bonferonni test ($p<0.05$) using a statistical package for the IBM PC, SAS Industries, Inc. (Cang, N.C.).

RESULTS

Figure 1B:
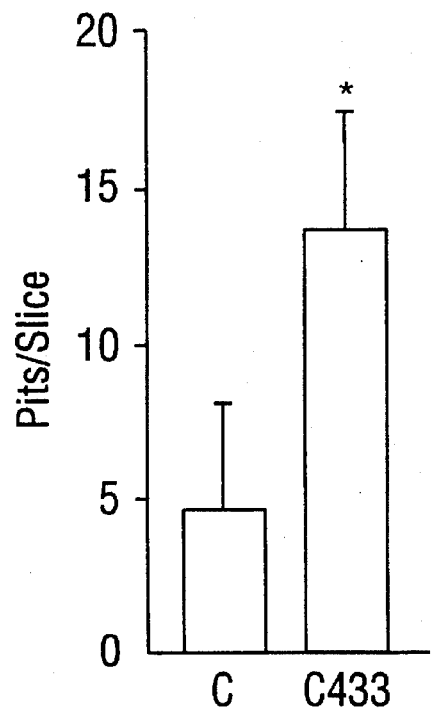

The conditioned media harvested from C433 cells stimulated freshly isolated neonatal rat osteoclasts to form resorption lacunae on sperm whale dentine. There was a 3-fold increase in resorbed area/dentine slice compared with controls, and the C433-conditioned medium contained similar resorbing activity to maximal concentrations of parathyroid hormone ($10^{-8}M$) in this assay (FIG. 1A.). The conditioned medium also stimulated giant cells isolated from human giant cell tumors of bone to form resorption lacunae on sperm whale dentine. These giant cells were isolated using a panning technique with an antibody, 23C6, which recognizes osteoclasts preferentially (Horton et al., 1985). The area of dentine resorbed by these giant cells was increased 180-fold over controls (FIG. 1B.). When conditioned medium from C433 cells was incubated with organ cultures of neonatal mouse calvariae previously incorporated with $^{45}Ca$, there was an increase in bone resorption. Thus, the conditioned medium harvested from C433 cells contains an activity which stimulates isolated osteoclasts to form resorption lacunae and stimulates bone resorption in organ cultures.

Figure 1C:
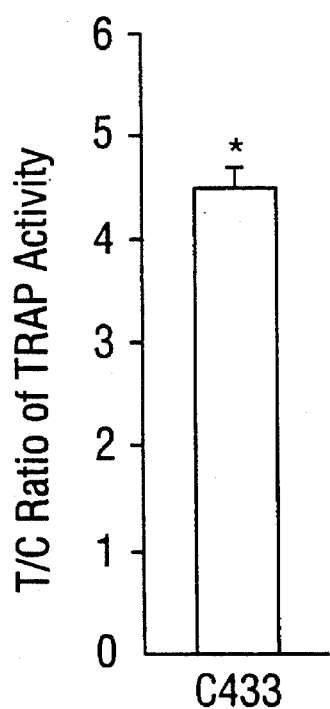
Figure 1D:
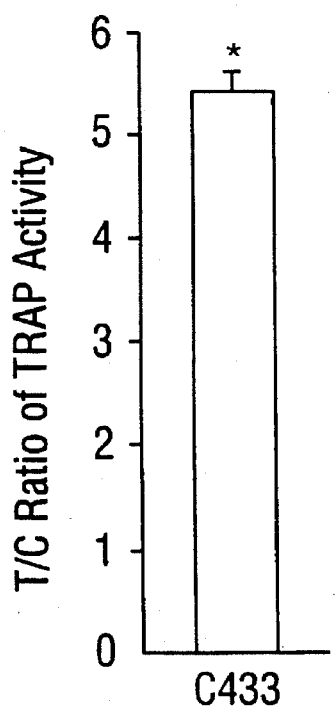

In order to characterize and identify the bone-resorbing activity produced by C433 cells, Tartrate-Resultant Acid Phosphatase (TRAP) activity in isolated purified avian osteoclasts was used as a measure of osteoclast stimulation. Measurement of pits on calcified matrices is time-consuming, difficult and imprecise, and is not suitable for a purification assay. TRAP activity has been used previously as a parameter of osteoclast stimulation (Chambers and Fuller, 1984; Zaidi et al., 1988; Oreffo et al., 1990, 1992). This measurement was used to assess the capacity of C433-conditioned medium to activate osteoclasts. Increases in TRAP activity of up to 5-fold were seen when C433-conditioned medium was added to isolated avian osteoclasts (FIG. 1C). Even greater increases in TRAP activity in response to C433-conditioned medium were seen in giant cells from giant cell tumors of bone (FIG. 1D). However, these could not be used to monitor purification, because they were obtained from surgical specimens, and tumor availability was not predictable.

Figure 2:
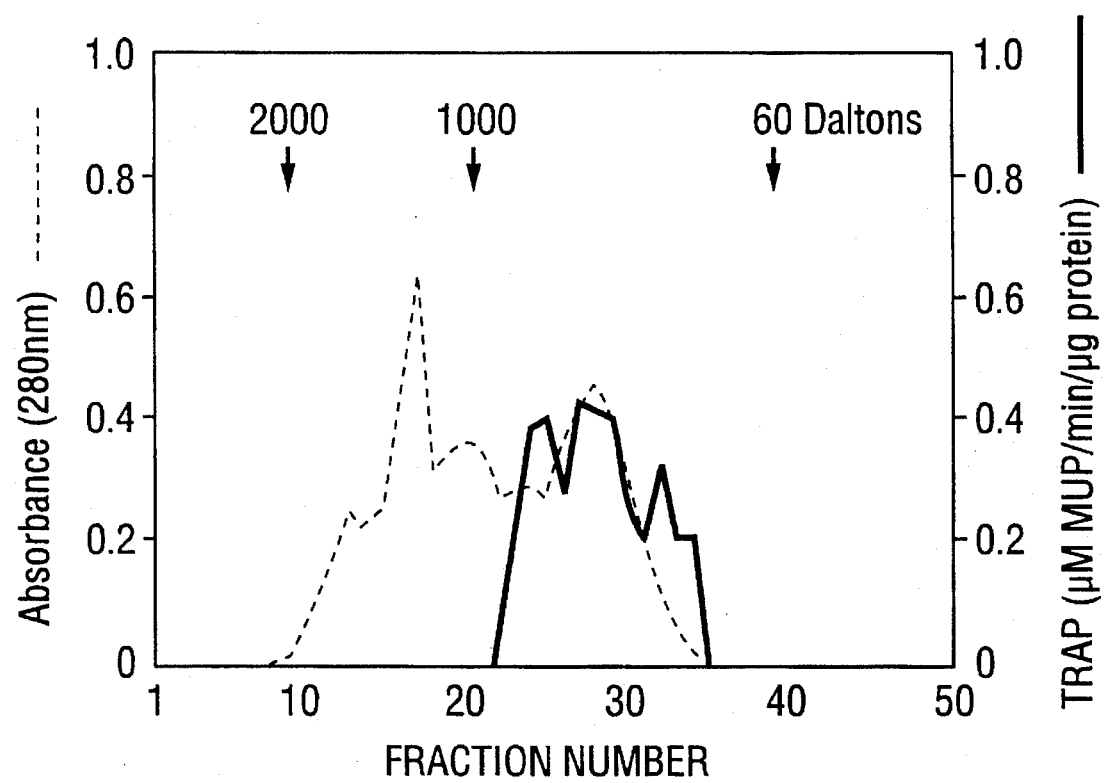
FIG. 2. Molecular mass determination of C433 activity. Fifty ml of C433-conditioned medium was filtered, lyophilized, and reconstituted before applying to a Bio-Gel P-2 column equilibrated in 10 mM ammonium bicarbonate, pH 7.1, and standardized (insulin >2000 daltons; nonapeptide, 986 daltons; and sodium chloride, 58.5 daltons). Protein was monitored at 280 nm. Every second fraction was bioassayed utilizing the isolated avian osteoclast TRAP assay. Molecular mass of the activity was determined to be less than 1000 daltons. MUP, methylumbelliferyl phosphate.

Using a combination of filtration membranes and gel filtration experiments, the activity was found to be present in fractions less than 5 kDa. FIG. 2 represents a Bio-Gel P2 column showing that the activity was eluted from this column between the markers for 1000 and 60 daltons.

Figure 3A:
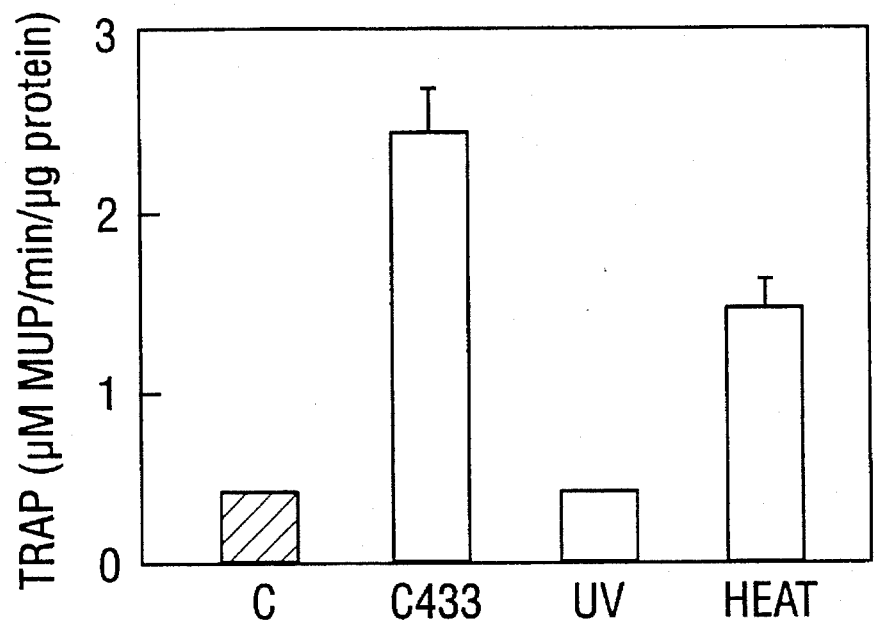
FIGS. 3A–3D. Chemical characterization of activity.
Figure 3B:
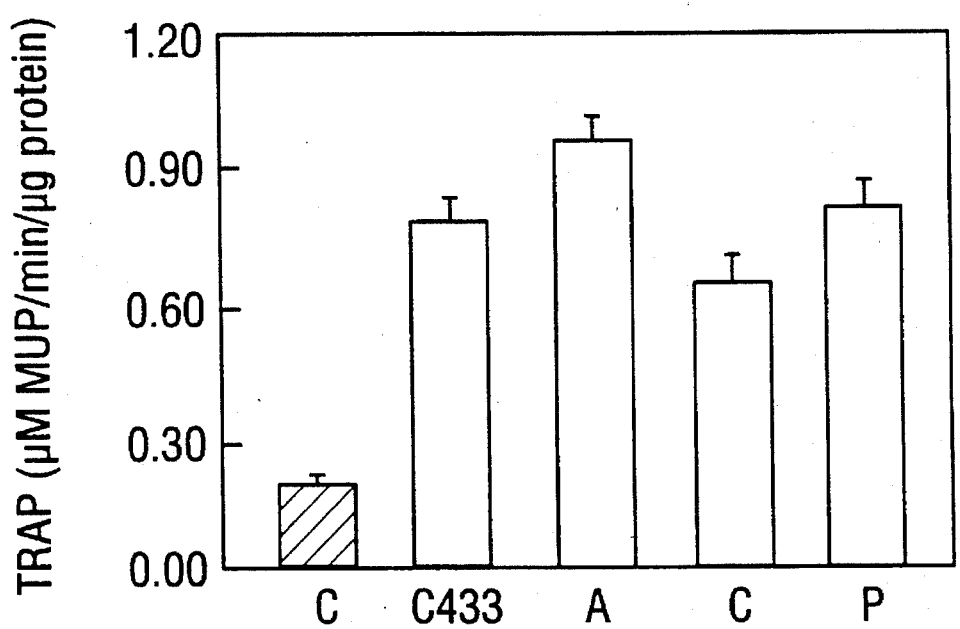
Figure 3C:
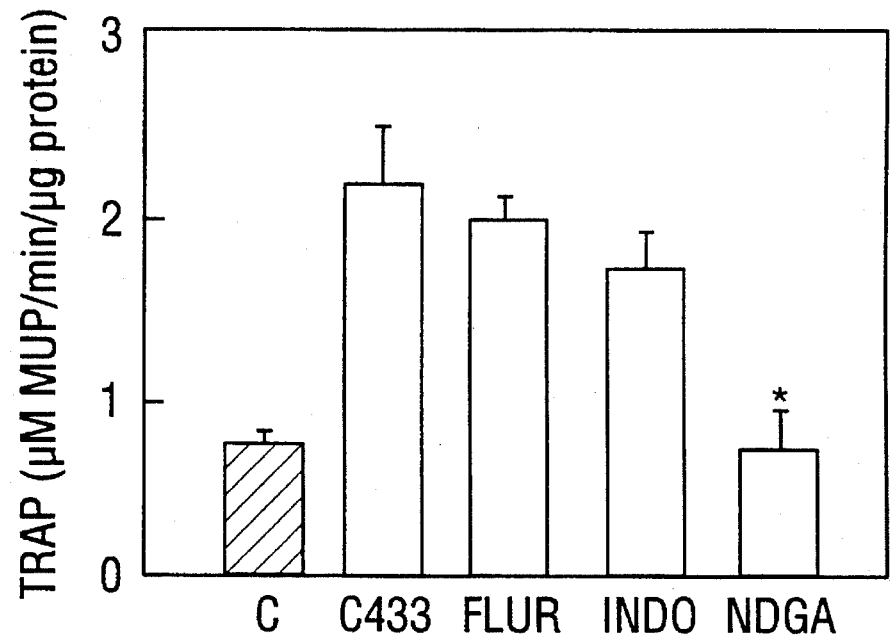
Figure 3D:
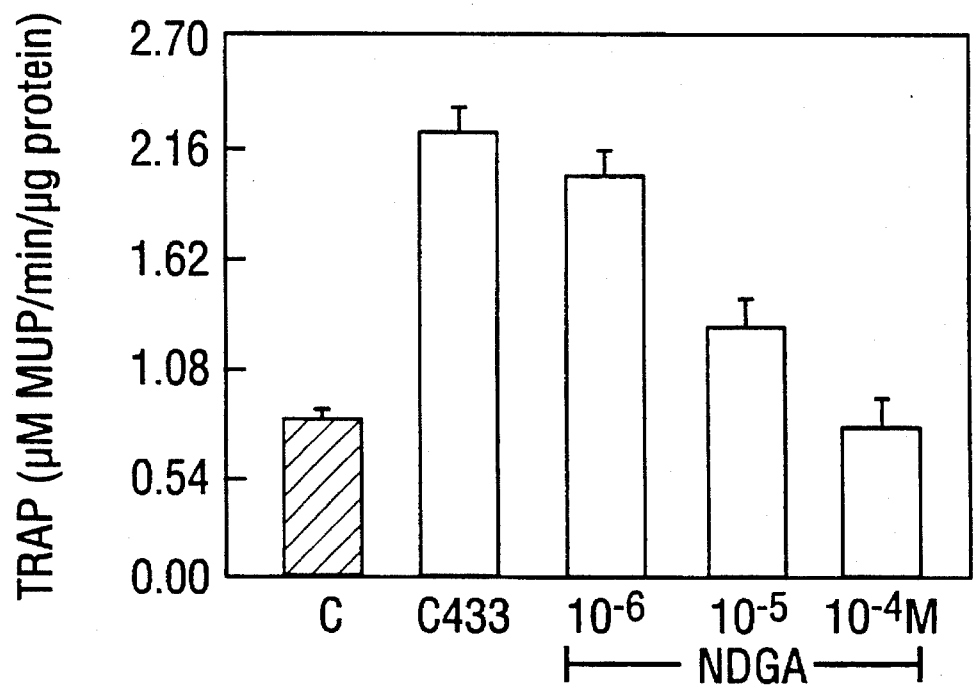

Further chemical characterization of the activity showed that it was relatively heat-stable but completely destroyed by 24 h of ultraviolet light treatment (FIG. 3A). The activity in C433 was not significantly affected by treatment with proteases such as aminopeptidase M, carboxypeptidase, or Pronase CB (FIG. 3B). The activity was extractable in ethyl acetate and appeared to behave as an organic molecule. Thus, the activity appeared to be a small nonprotein compound. Since prostaglandins and other arachidonic acid metabolites possess these characteristics and are known to have important effects on bone cell function, it was determined whether arachidonic acid metabolites could be responsible. The initial approach was to determine if production of the activity by C433 cells was blocked by inhibitors or arachidonic acid pathway enzymes. These included flurbiprofen and indomethacin which inhibit prostaglandin synthase, and nordihydroguaiaretic acid, and inhibitor of the lipoxygenases. Flurbiprofen ($10^{-5}$M) and indomethacin ($10^{-6}$M) had no significant effects on production of C433 activity (FIG. 3C). The lipoxygenase inhibitor nordihydroguaiaretic acid completely blocked production of C433 activity in a dose-dependent manner (FIGS. 3C and 3D).

Figure 4A:
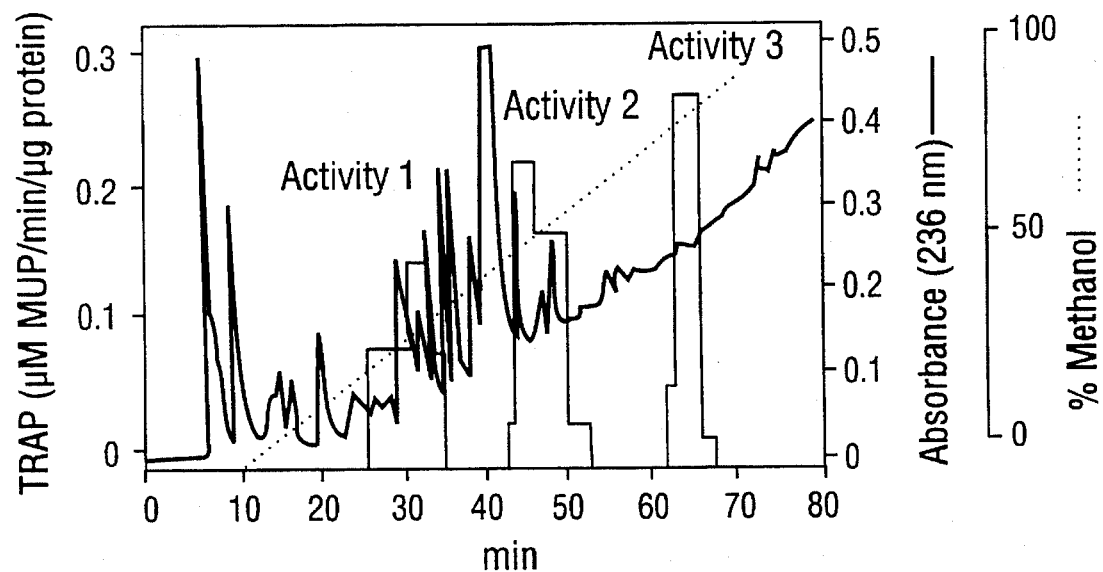
FIGS. 4A–4C. Partial purification of biological activity from C433-conditioned medium using C$_8$ reverse phase high pressure liquid chromatography (FIG. 4A). The gradient was 0–100% methanol, 1% acetic acid over 60 min with 6-ml fractions collected. The fractions were dried under nitrogen, and those fractions to be used for bioassay (TRAP induction in avian osteoclasts) were stabilized with 20 µl of 10% bovine serum albumin. Fractions to be used for GC-MS analysis were immediately derivatized.
Figure 4B:
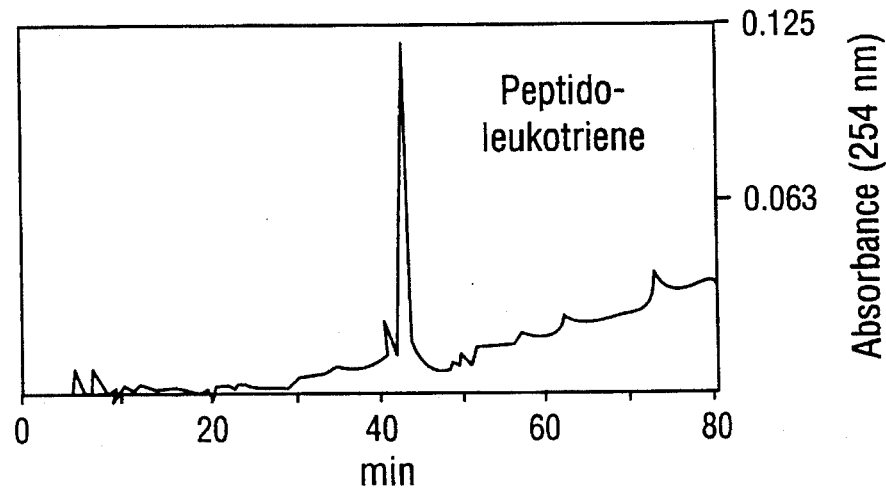
Figure 4C:
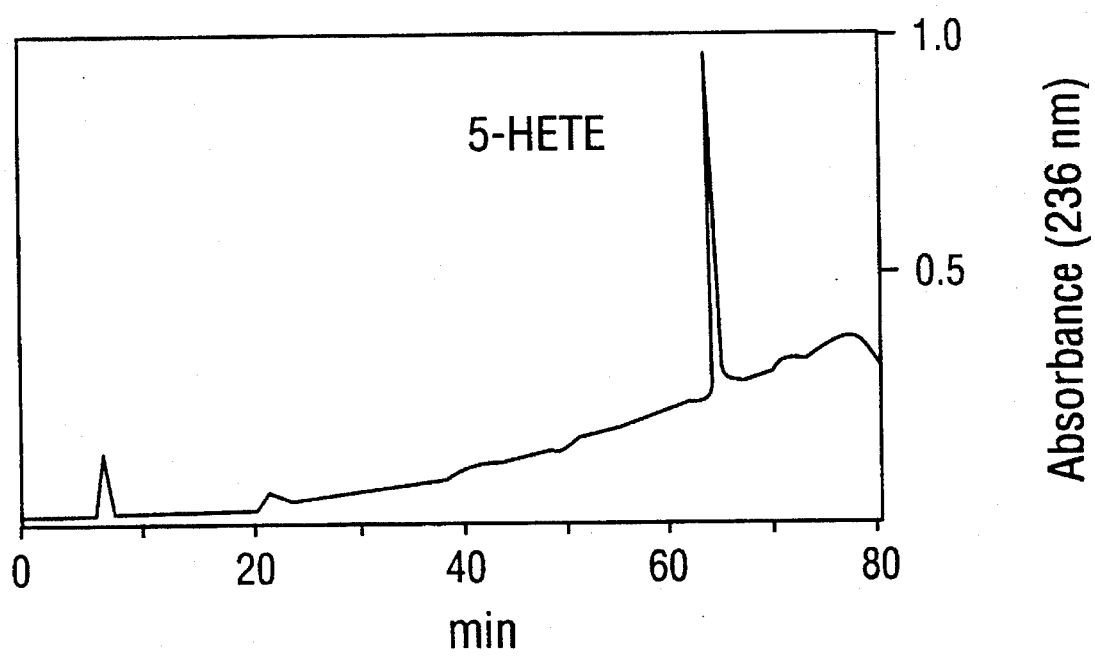
Figure 5A:
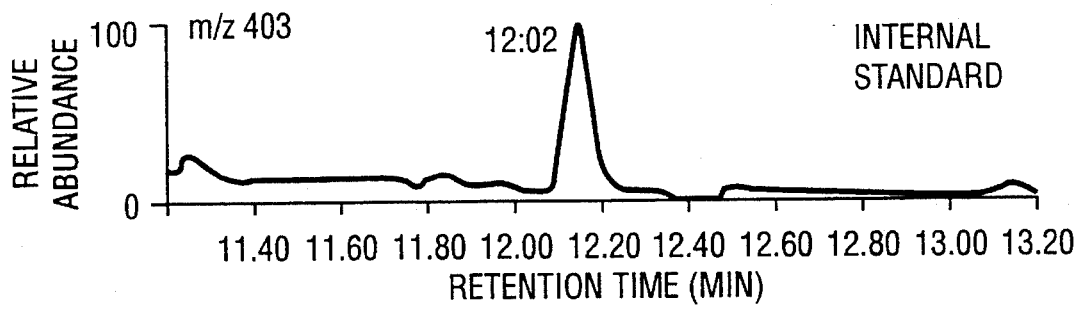
FIG. 5. Stable isotope dilution/gas chromatography-mass spectrometry analyses of HPLC fractions exhibiting osteoclast activating activity. [$^{13}$C$_4$]LTC$_4$ (0.5 ng) was added to each fraction which was then hydrogenated and converted to the pentafluorobenzyl ester trimethylsilyl ether derivative. Ions monitored during GC-MS analysis corresponded to the product of the endogenous 5-LO metabolites (m/z 399) and the internal standard (m/z 403). The slightly shorter retention time observed during analysis of the activity 1 fraction reflected a minor difference in analytical conditions. The relative abundance of the m/z 399 ion was normalized for each analysis to the relative abundance of m/z 403. For quantification, response rations (m/z 399 to m/z 403) were based on peak area calculation.
Figure 5B:
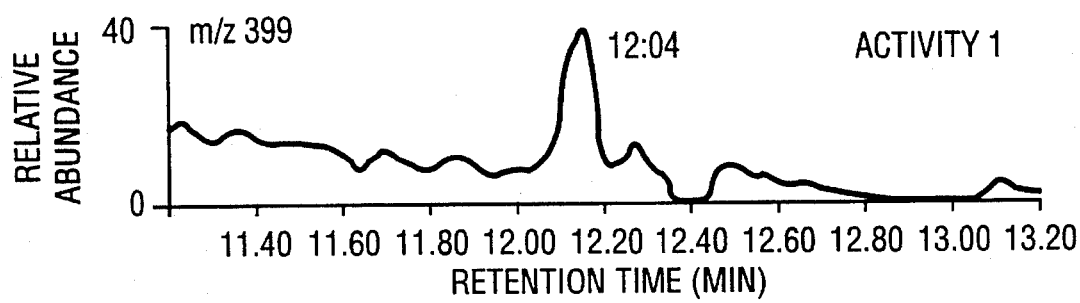
Figure 5C:
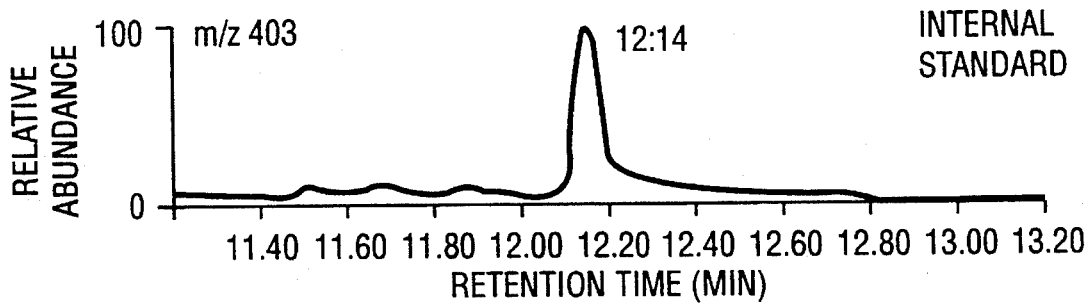
Figure 5D:
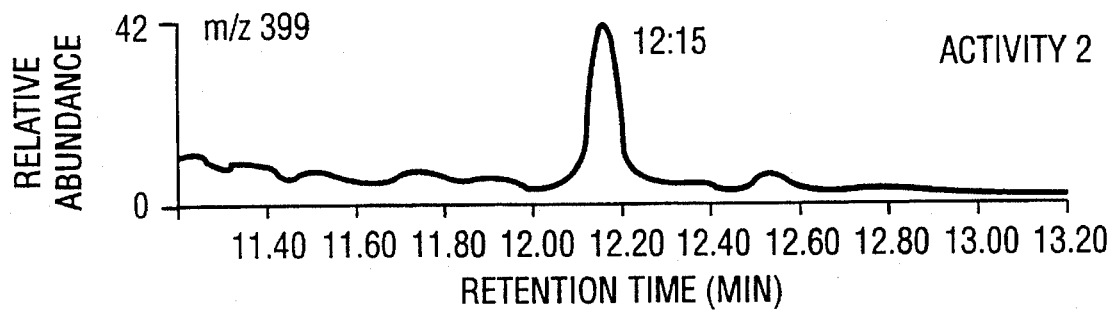
Figure 5E:
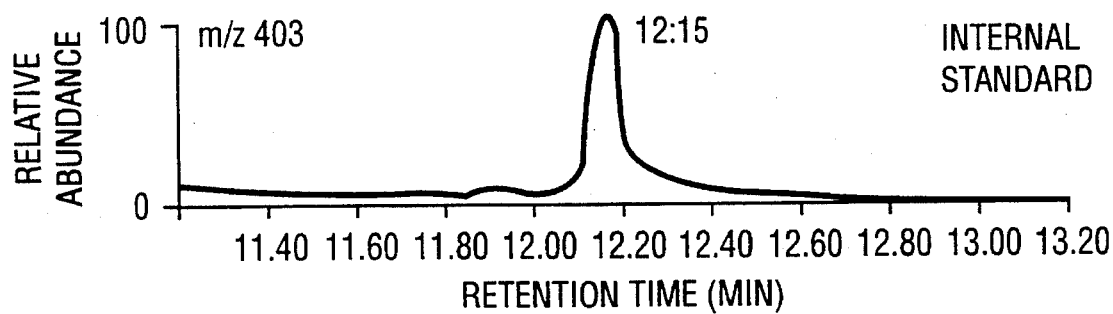
Figure 5F:
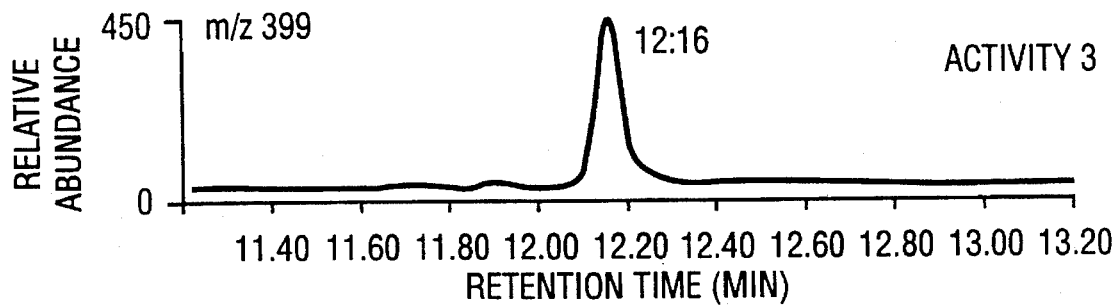

Since 5-LO inhibition studies implicated 5-LO metabolites as mediators of osteoclast activation, a purification protocol was devised for lipoxygenase metabolites of the arachidonic acid pathway. Stability of the factors was examined in various solvents useful for HPLC purification. The activity was stable in ethanol and methanol but not in triethanolamine or pyridine. Acetonitrile was found to be toxic to isolated osteoclasts even after repeated lyophilization, and so methanol was used for HPLC. After purification using HPLC, bioactivity was observed in unretained material and in three fractions corresponding to fraction numbers 9 and 10 (activity 1=25% MeOH), fraction numbers 17 and 18 (activity 2=55% MeOH) and fraction number 25 (activity 3=85% MeOH) (FIG. 4A–4C).

The concentrations of 5-LO metabolites in each HPLC fraction were determined by stable isotope dilution and gas chromatography-mass spectrometry (GC-MS) after hydrogenation and conversion to pentafluorobenzyl ester trimethylsilyl ether derivatives. Ions characteristic of the product of endogenous 5-LO metabolites (m/z 399) and of the internal standard, [$^{13}C_4$]LTC$_4$ (m/z 403), were monitored during each analysis. Thus, identification of endogenous 5-LO products was based on the observation of the characteristic ion at the appropriate chromatographic retention time, defined by the internal standard. The results (FIG. 5) were consistent with the presence of 5-LO metabolites in each of the HPLC fractions exhibiting osteoclast activating activity at amounts corresponding (in "LTC$_4$ equivalents") to 35, 83, and 917 pg/ml for the 25, 55, and 85% fractions, respectively.

A commercially available mixture of LTC$_4$/LTD$_4$ was applied to the C$_8$ reverse phase HPLC column under the same conditions as the extracted C433-conditioned medium. LTC$_{4/LTD4}$ eluted in the same fraction as activity 2 (FIG. 4B). Commercial available 5-HETE was also applied to C$_8$ reverse phase HPLC under the same conditions as the extracted C433-conditioned medium. 5-HETE eluted in the same fraction as activity 3 (FIG. 4C). The data are therefore consistent with the identification of activity 3, the 85% peak, as 5-HETE and activity 2, the 55% peak, as a peptido-leukotriene, either LTC$_4$, -D$_4$ or -E$_4$. Activity 1, the 25% peak, remains unidentified. Commercially available LTB$_4$ elutes at 80% MeOH, and LTB$_4$ was not detectable in any fraction by GC/MS analysis.

To confirm that C433-conditioned medium contained these 5-LO metabolites and that production was hormonally regulated, radioimmunoassays were performed for 5-HETE using commercially available kits. C433 cells secreted large amounts of 5-HETE (Table I) and 1,25-(OH)$_2$ vitamin D$_3$ increased the production of 5-HETE by C433 cells over control levels.

TABLE I

Quantitation of 5-HBTE in C433-conditioned media with and without treatment with 1,25-(OH)$_2$ vitamin D$_3$ ($10^{-8}$ M) A radioinmunoassay (Advanced Magnetics, Inc., Cambridge, MA) was performed to measure 5-HETE in C433 conditioned media. Units are in pg/ml. Assays were performed in duplicate.

| Time | No treatment | +1,25-(OH)$_2$ vitamin D$_3$ ($10^{-8}$ M) |
|---|---|---|
| h | | |
| 0 | 0.62, 0.51 | |
| 6 | 0.91, 0.90 | 3.36, 3.53 |
| 12 | 4.98, 5,71 | 11.07, 11.68 |

Figure 6A:
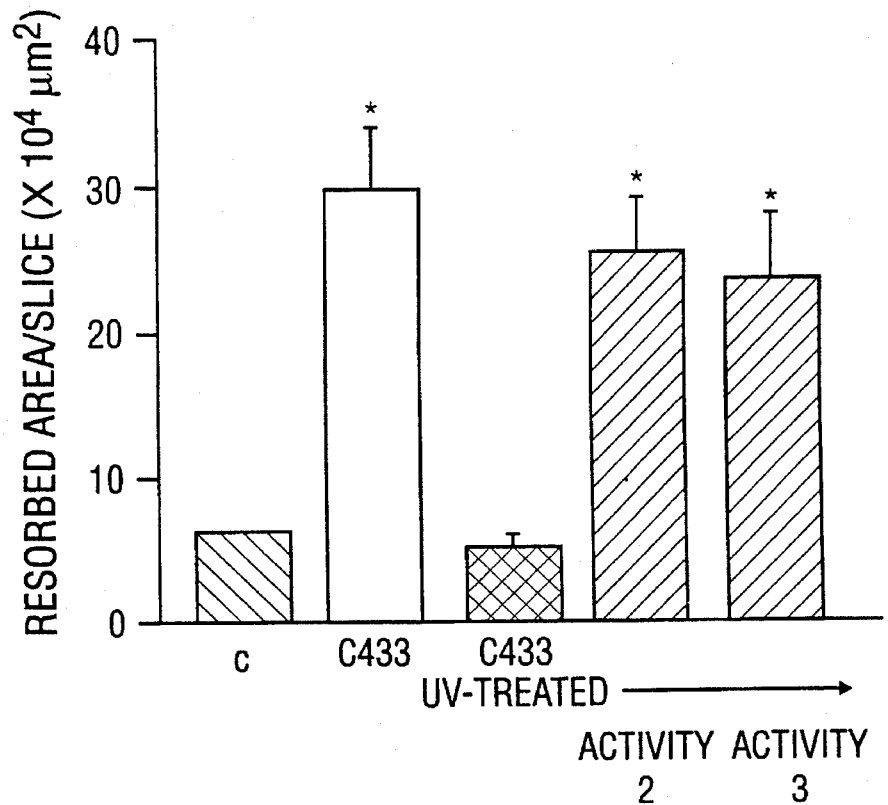
FIGS. 6A–6B. UV-treated C433-conditioned medium (CM) stabilized the HPLC-purified activity 2 and activity 3 fractions as determined in the isolated rat osteoclast pit formation assay.
Figure 6B:
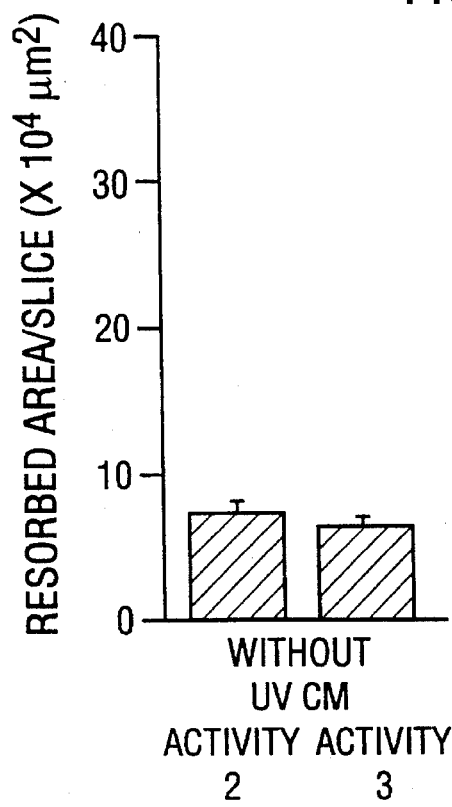
Figure 7A:
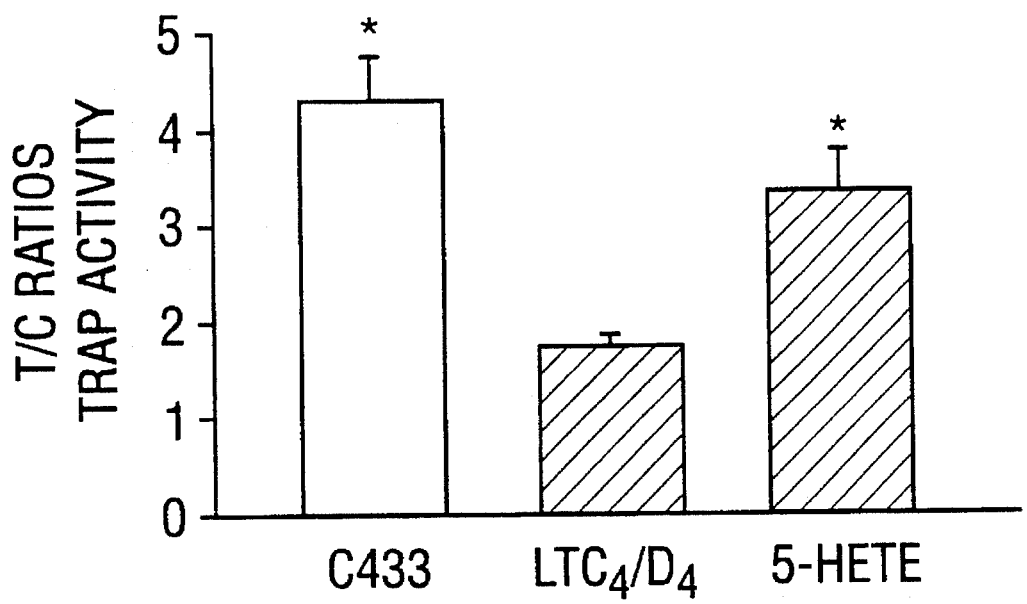
FIGS. 7A–7D. Biological effects of commercially available peptido-leukotrienes and 5-HETE. LTC$_4$/Ltd$_4$ ($10^{-10}$M) and 5-HETE ($10^{-10}$M) were incubated for 48 h in the presence of isolated avian osteoclasts (FIG. 7A), isolated 23C6(+) human giant cells of bone (FIG. 7B), and TRAP induction was measured. LTC$_4$ ($10^{-10}$ M) was tested on pit formation by isolated 23C6+ human giant cells (FIG. 7C) and LTE$_4$ ($10^{-10}$M) on pit formation by isolated rat osteoclasts (FIG. 7D). *, significant difference using Bonferonni ($p<0.05$). PTH, parathyroid hormone.
Figure 7B:
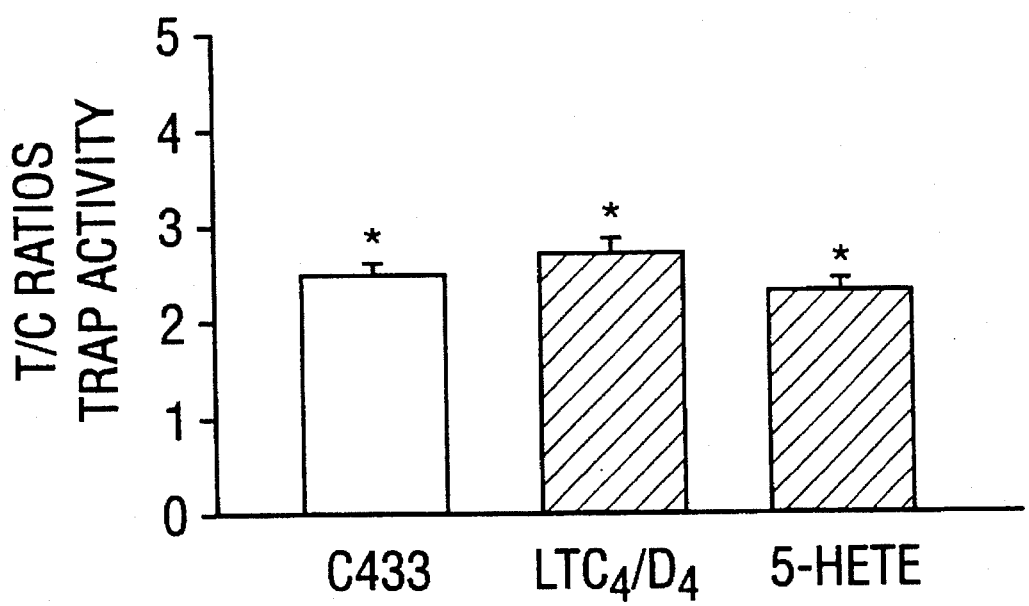
Figure 7C:
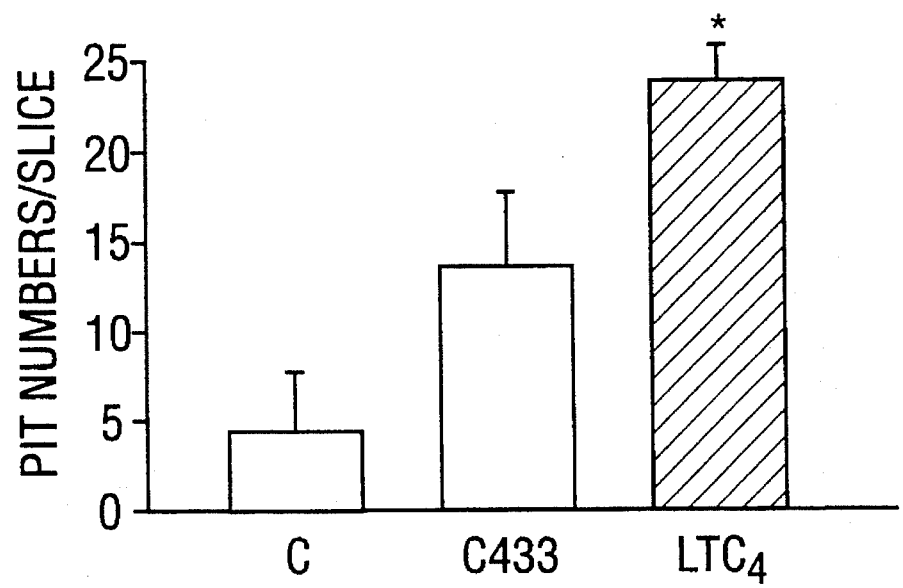
Figure 7D:
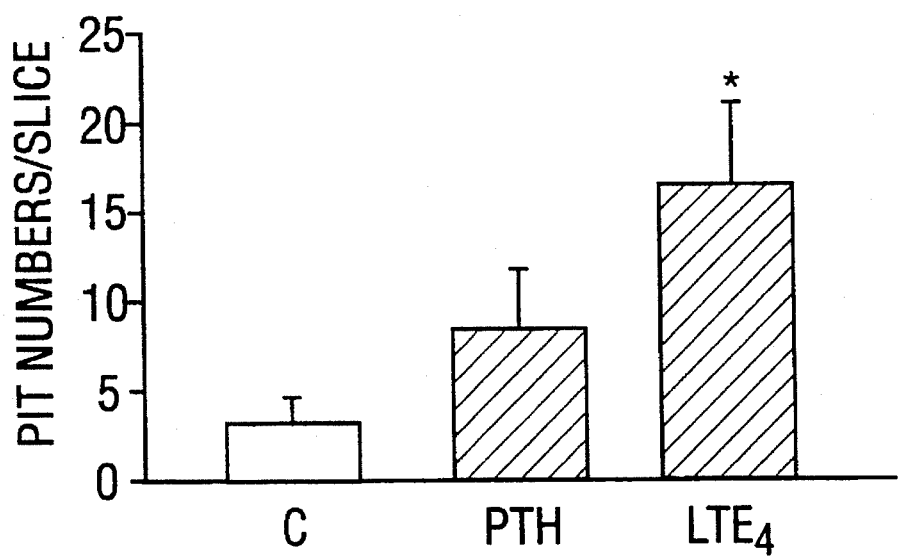

When activity 2 (putative peptido-leukotriene) and activity 3 (putative 5-HETE) were added to the isolated rat osteoclast pit assay in UV-treated C433 conditioned medium, they stimulated bone resorption in a manner similar to that of the untreated C433-conditioned medium (FIGS. 6A–6B). Commercially available LTC$_4$/LTD$_4$ and 5-HETE were then tested on both isolated avian osteoclasts and isolated human giant cells. With both avian osteoclasts and human giant cells, LTC$_4$/LTD$_4$ and 5-HETE at $10^{-10}$M maximally stimulated TRAP activity (FIGS. 7A and 7B). Commercially available LTC$_4$ and LTE$_4$ were tested for capacity to stimulate pit formation by isolated giant cells (FIG. 7C) and isolated rat osteoclasts (FIG. 7D). Both compounds stimulated isolated resorbing cells at $10^{-10}$M. These commercially available metabolites were also tested in the murine neonatal calvaria assay and the fetal rat long bone assay, both well recognized assays for measuring the effects of bone-resorbing cytokines. The metabolites induced resorption in the neonatal murine calvarial assay but not the fetal long bone assay (data not shown), the same results as that observed with the C433-conditioned medium (Oreffo et al., 1991).

Figure 8A:
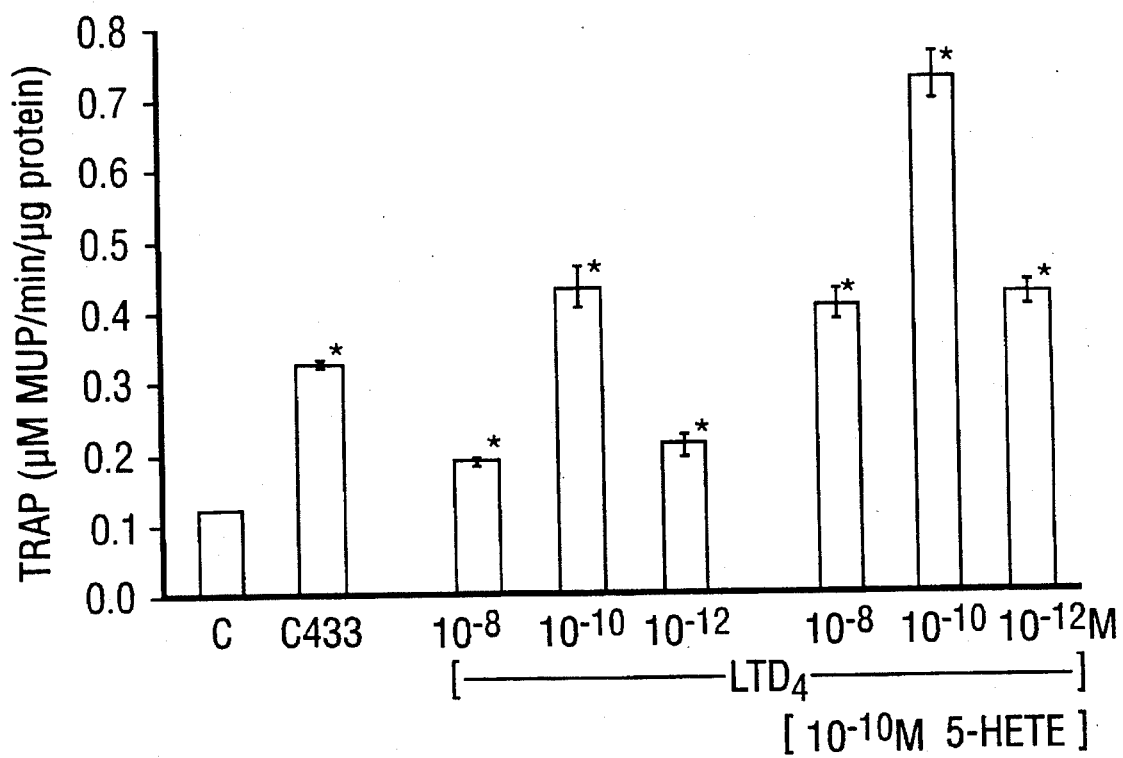
FIG. 8A shows the effect of LTB$_4$ on $^{45}$Ca release in the mouse calvarial assay.
Figure 8B:
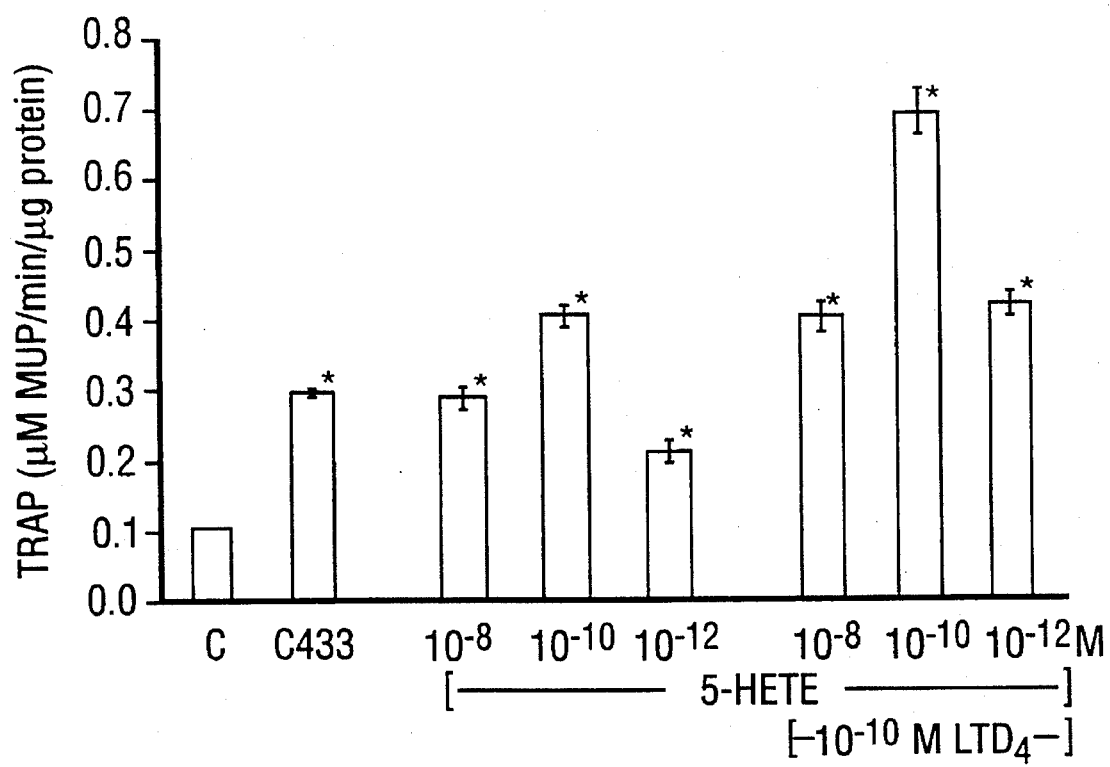
FIG. 8. Effect of combining commercially available 5-HETE and the peptido-leukotriene LTD$_4$ on TRAP activity in isolated avian osteoclasts. Both 5-HETE and LTD$_4$ optimally stimulated TRAP activity at $10^{-10}$M. Higher molarity ($10^{-8}$M) appears to stimulate suboptimally. The effects of combining 5-HETE and LTD$_4$ appear additive.
Figure 8C:
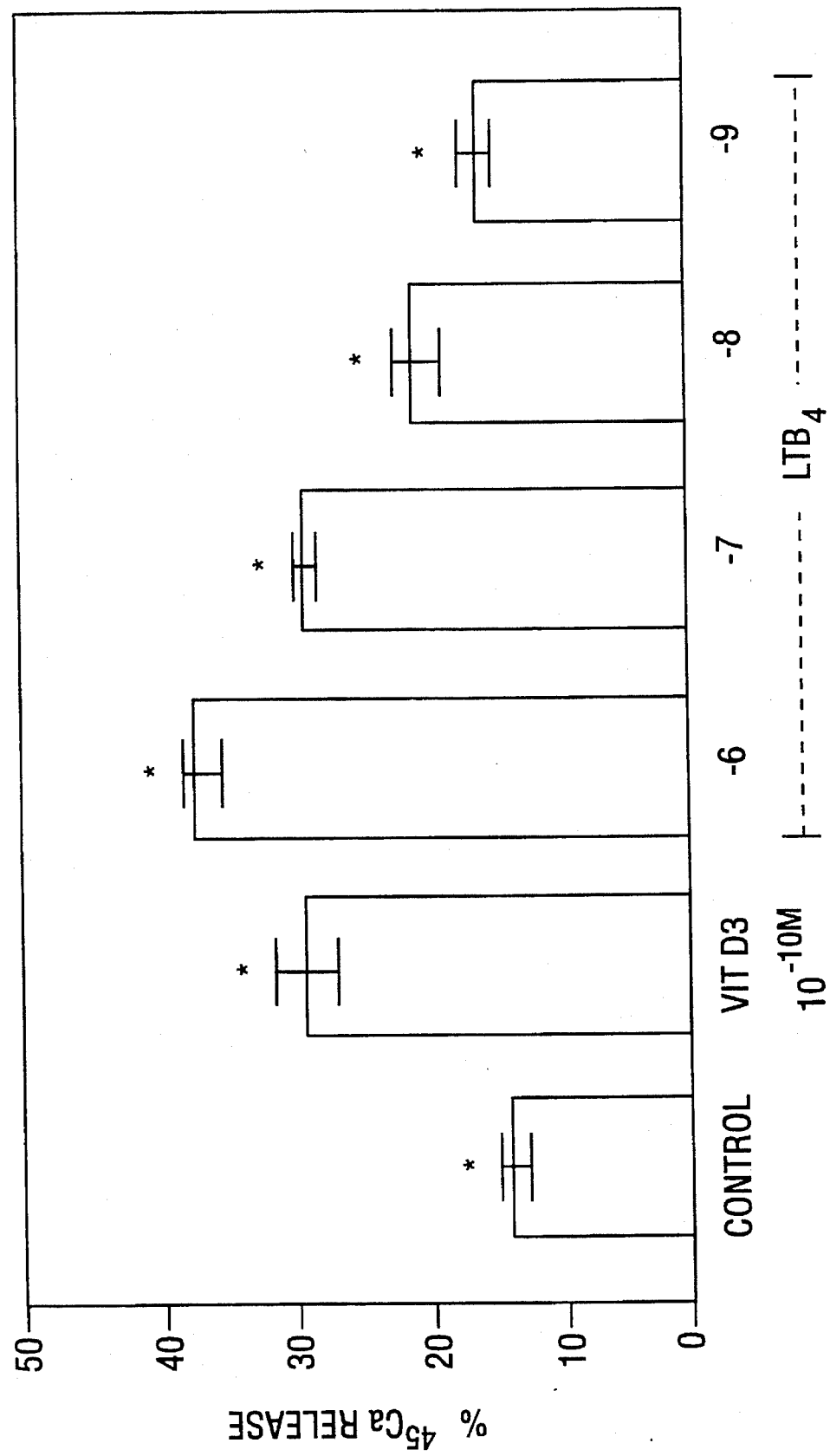
Figure 9:
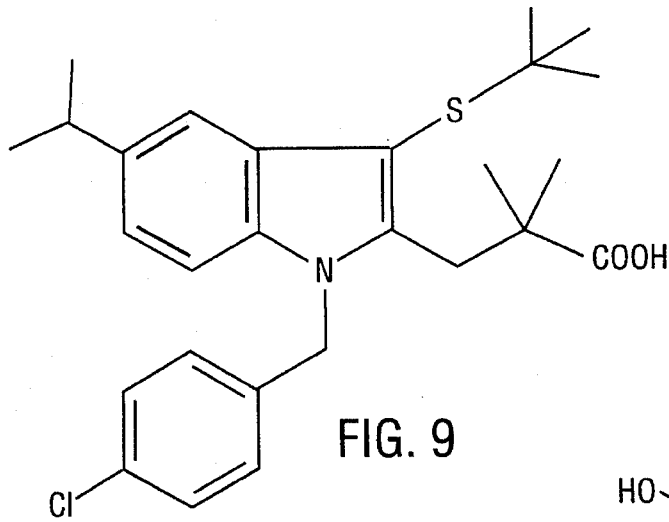
FIG. 9 shows the structure of NDGA.
Figure 10:
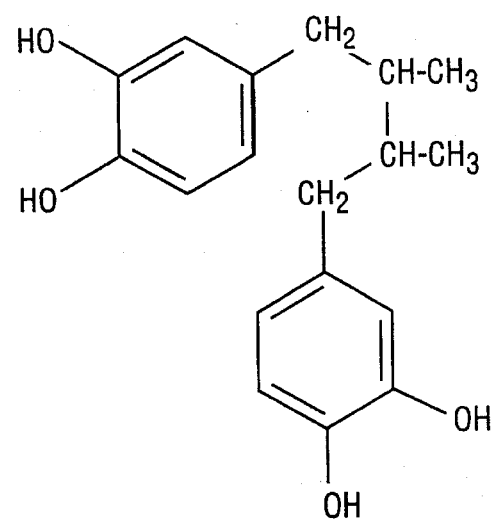
FIG. 10 shows the structure of MK886.
Figure 11:
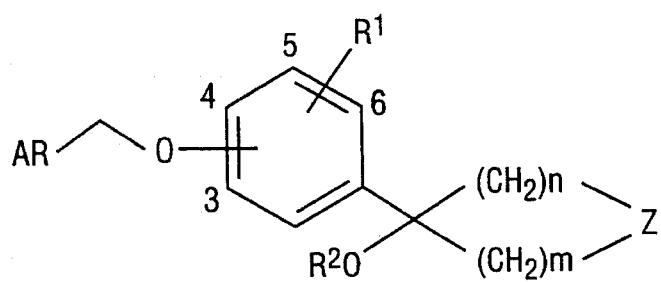
FIG. 11 shows the structure of ZM 230,487 (1-ethyl-6-[fluoro-5-(4-methoxy-3,4,5,6-tetrahydro-2H-pyran-4-yl)phenoxy]methyl-quinol-2-one).
Figure 12A:
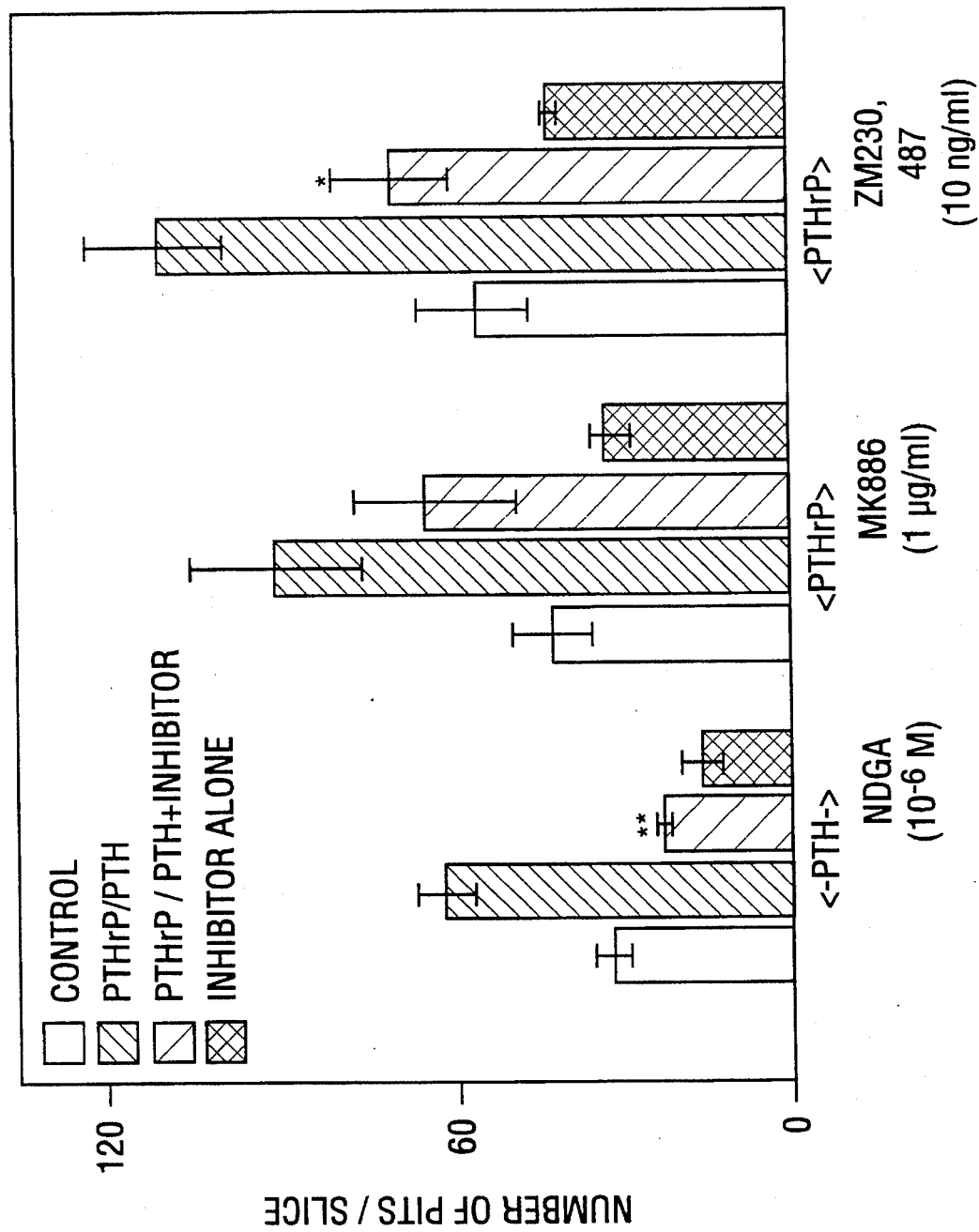
FIG. 12A shows the effects of NDGA ($10^{-6}$M), MK886 (1 µg/ml) and ZM 230,487 (10 ng/ml) on isolated rat osteoclasts. The cells were cultured in the presence of factor and 5-LO inhibitor for 20 hours before harvest. Data are expressed in number of pits per dentine slice.
Figure 12B:
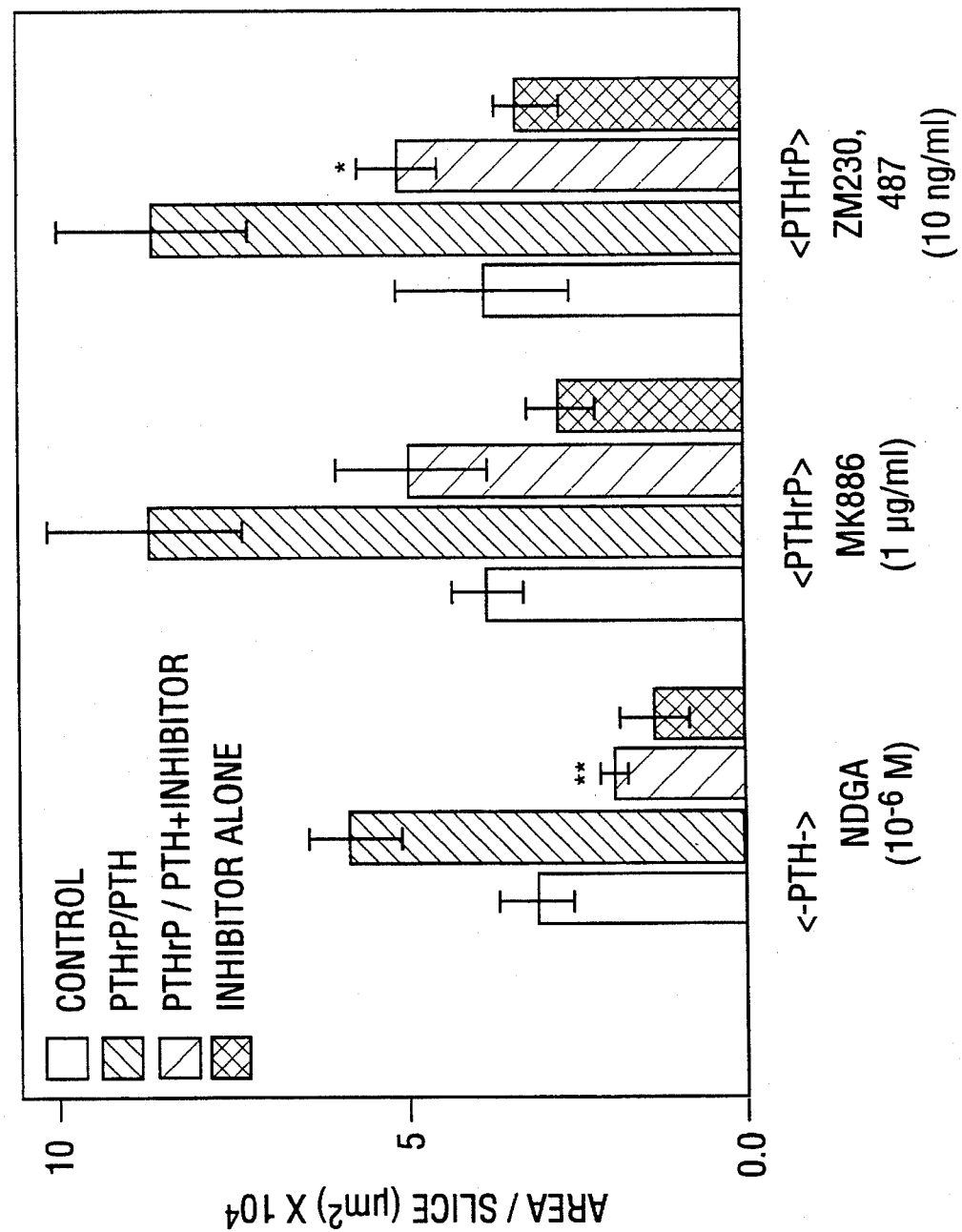
FIG. 12B shows data expressed as area of resorption lacunae per dentine slice.
Figure 12C:
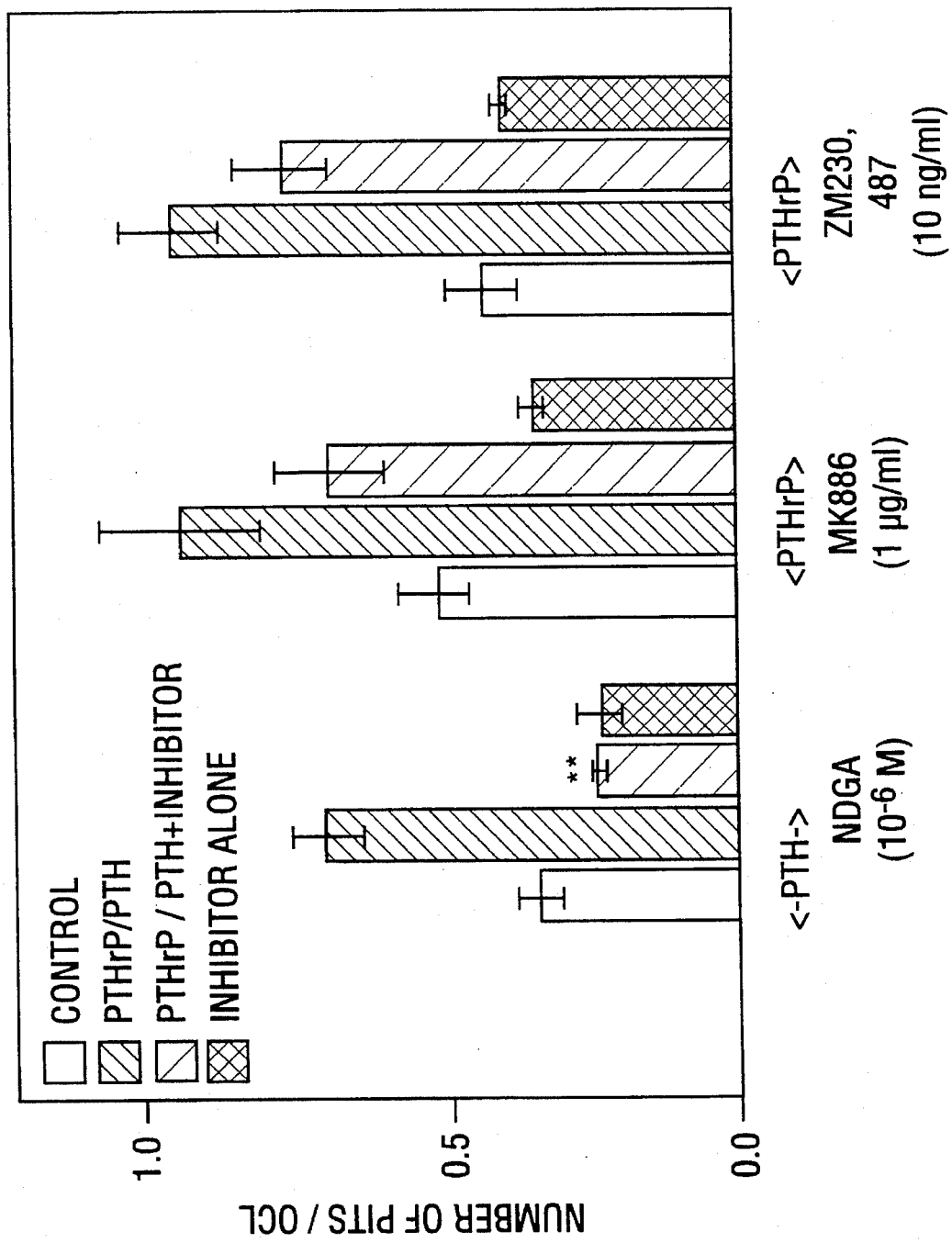
FIG. 12C shows the number of resorption lacunae per osteoclasts.
Figure 12D:
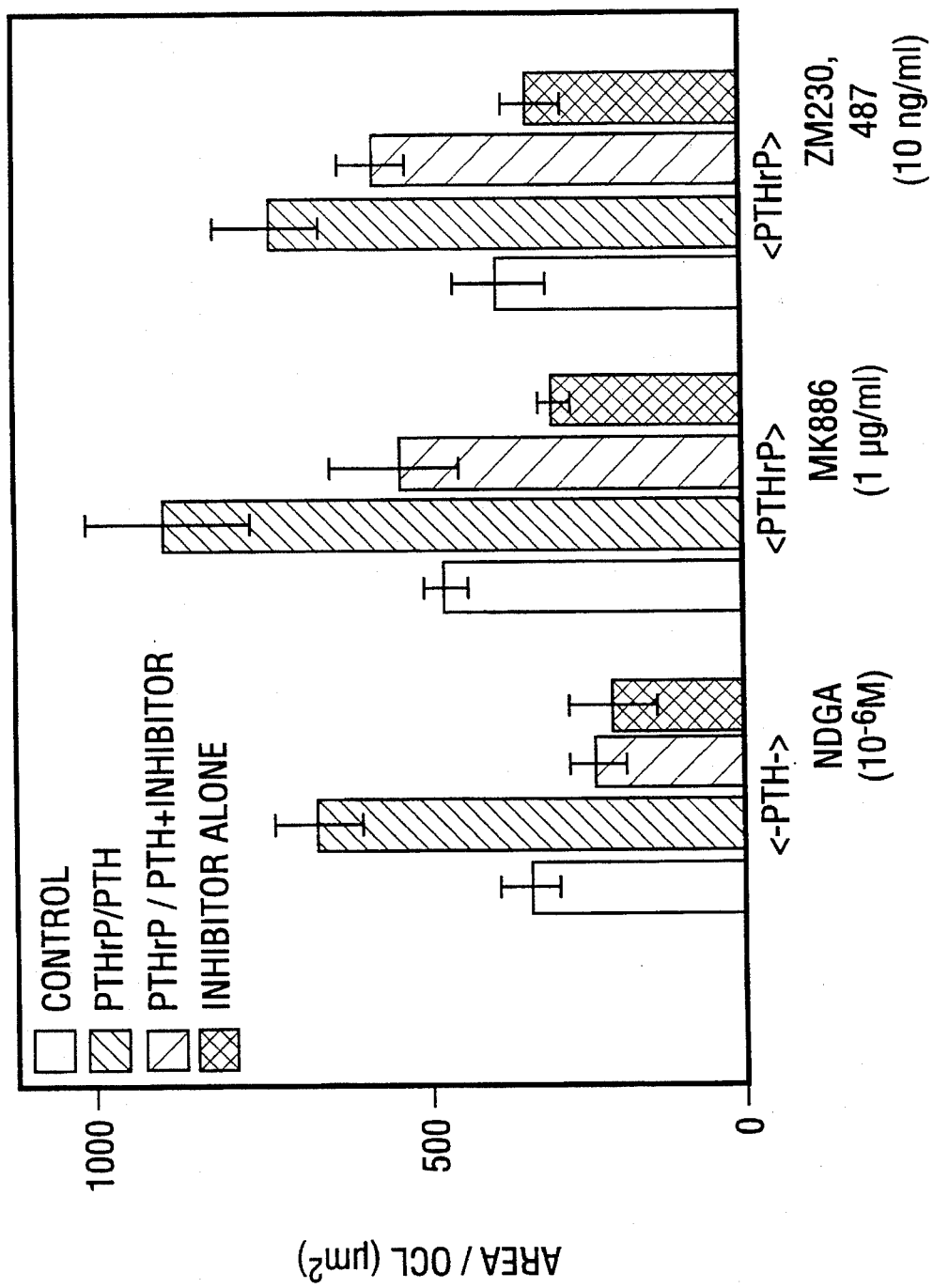
FIG. 12D shows the area of resorption lacunae per osteoclast.

To determine whether 5-HETE and the peptido-leukotrienes have additive or synergistic biologic effects, commercially available compounds were tested for TRAP induction in isolated avian osteoclasts. The effects are not synergistic but appear additive (FIG. 8).

The bone-resorbing activity found in conditioned medium from a stromal cell line isolated from a giant cell tumor of bone (C433) can be ascribed to metabolites of the 5-lipoxygenase pathway. These metabolites were purified from the conditioned medium of C433 cells, using an osteoclast stimulation assay. Commercially available 5-LO metabolites mimicked the effects of C433-conditioned medium, LTC$_4$/LTD$_4$, 5-HETE, and C433-conditioned medium caused pit formation by isolated rat osteoclasts and human giant cells and stimulated bone resorption in neonatal mouse calvariae. They also stimulated TRAP activity in avian osteoclasts and human giant cells.

Leukotriene ($LTB_4$) was tested in the mouse calvarial assay and found to stimulate osteoclastic bone resorption even though it was not detected in the C433 conditioned media. FIG. 8A shows a dose response effect for $LTB_4$ in the mouse calvarial assay where $10^{-8}$ to $10^{-6}$M $LTB_4$ showed a statistically significant degree of resorption stimulation.

Eicosanoids are derived from the oxidative metabolism of arachidonic acid (Smith, 1989; Parker, 1987). These derivatives, which include the prostaglandins, the hydroxyeicosatetraenoic acids, and the leukotrienes are diverse and have powerful but short-lived physiological effects. It has been well documented that prostaglandins play a critical role in both bone resorption and bone formation (Raisz and Martin, 1983), but little is known concerning the role of leukotrienes in bone remodeling. Prostaglandins such as prostaglandin $E_1$ and prostaglandin $E_2$ in general are more stable than the leukotrienes and have been shown to inactivate isolated osteoclasts (Chambers and Dunn, 1983).

The C433-conditioned medium maintained activity when stored at 4° C. for 3–4 months. However, once purification was initiated, biological activity was quickly lost, especially after HPLC purification. The studies suggest the presence of a stabilizing factor in C433-conditioned medium.

This data indicate that 5-lipoxygenase metabolites stimulate isolated osteoclasts to resorb bone in vitro and may represent a mechanism by which mononuclear cells in human giant cell tumors communicate with the giant cells. In addition, these results may explain a possible mechanism for communication between accessory cells and osteoclast activation in normal bone resorption. The analytic evidence supports the presence of peptido-leukotriene and 5-HETE, the latter being quantitatively more significant in C433-conditioned medium. The unknown eicosanoid is present in much smaller amounts and may prove difficult to identify as much larger volumes of conditioned medium will be necessary.

EXAMPLE 2

Fetal Rat Long Bone Assay

Fetal rat long bone assays were performed as previously described (Garrett et al, 1990). Briefly, pregnant rats were injected with 200 µCi of $^{45}Ca$ on the 18th day of gestation. The following day the mothers were euthanized and fetuses removed. The mineralized shafts of the radii and ulnae are dissected free of cartilaginous tissue and incubated in BGJb media for 24 hours at 37° C. in a humidified atmosphere of 5% $CO_2$ to allow for the exchange of loosely bound $^{45}Ca$ with stable calcium in the media. Bones were cultured for a further 48 hours to 120 hours in BGJb media supplemented with 1 mg/ml bovine serum albumin with penicillin and streptomycin (RIA grade, Sigma, St. Louis, Mo.) in the presence of test or control substances. Bone resorbing activity was expressed as the percentage of the total $^{45}Ca$ released into the media.

EXAMPLE 3

Isolated Fetal Rat Osteoclasts Assay

Quantitation of the effects of isolated neonatal rat osteoclasts on calcified matrices was determined using minor modifications of the disaggregated osteoclast resorption assay as described by Boyde et al (1984). Briefly rat osteoclasts isolated as described by Chambers et al. (1983) were dispersed on prewetted (αMEM plus 5% FBS) slices of sperm whale dentine. Cultures were performed in 48 well-microtiter plates in humidified air (10% $CO_2$) at 37° C. in αMEM medium (one slice/well in 200 µl medium). Numbers of osteoclasts and resorption lacunae were quantitated as described above for the avian osteoclasts.

EXAMPLE 4

Effects of NDGA on Factor Induced Bone Resorption in the Murine Calvarial Assay As illustrated in Table II, the murine calvarial assay described in Example 1 was conducted to illustrate the effects of NDGA on factor-induced bone resorption.

TABLE II

Effects of NDGA on Factor-Induced Bone Resorption in the Murine Calvarial Assay

| Factor/Conc.) | Control | NDGA $10^{-5}$M | Factor | Factor + NDGA | % Inhibition |
|---|---|---|---|---|---|
| IL-1/5 × $10^{-10}$M | 12.1 ± 0.7 | 10.6 ± 0.5 | 31.2 ± 1.4 | 24.6 ± 1.6* | 32.8 |
| | 13.4 ± 0.4 | 14.4 ± 0.9 | 27.7 ± 1.2 | 23.4 ± 1.4* | 30.0 |
| TNP/2 × $10^{-10}$M | 16.9 ± 1.3 | 14.2 ± 1.0 | 36.1 ± 2.3 | 27.8 ± 1.7* | 43.2 |
| | 16.4 ± 0.8 | 16.0 ± 1.8 | 39.7 ± 1.9 | 31.9 ± 1.5* | 33.5 |
| Lymphotoxin/5 × $10^{-9}$M | 18.2 ± 0.7 | 15.7 ± 0.5 | 35.0 ± 1.5 | 26.8 ± 1.3* | 48.8 |
| | 19.8 ± 2.6 | 17.4 + 1.3 | 42.8 ± 1.2 | 35.5 ± 1.8* | 31.7 |
| PTH/4 ng/ml | 16.0 ± 0.9 | 15.0 ± 0.9 | 37.0 ± 1.4 | 30.6 ± 1.8 | 30.5 |
| | 14.7 ± 0.4 | 13.0 ± 1.1 | 39.9 ± 2.3 | 31.2 ± 0.9* | 34.5 |
| | 15.7 ± 0.6 | 12.8 ± 1.3 | 29.8 ± 2.9 | 28.6 ± 2.7 | 8.5 |
| 1,25$D_3$/$10^{-10}$M | 16.9 ± 1.3 | 14.2 ± 1.0 | 35.3 ± 1.5 | 31.7 ± 2.7 | 19.6 |
| | 18.7 ± 1.3 | | 31.8 ± 2.2 | 29.2 ± 3.9 | 19.8 |
| | 16.0 ± 0.9 | 15.0 ± 0.9 | 37.0 ± 1.4 | 32.5 ± 1.4 | 24.1 |

*=significantly different; p < 0.05. (As also in later tables.)

These data show that NDGA significantly inhibits bone resorption due to the factors: interleukin-1 (IL-1), tumor necrosis factor (TNF) and lymphotoxin. One out of three experiments showed significant inhibition of parathyroid hormone (PTH)-induced resorption but no significance was observed for 1,25(OH)$_2$ vitamin $D_3$-induced resorption.

EXAMPLE 5

Effects of NDGA on LPS-Induced Bone Resorption in the Murine Calvarial Assay Bacterial lipopolysaccharide (LPS) is known to induce bone resorption and may be particularly relevant in certain inflammatory conditions. The effects of NDGA on lipopolysaccharide-induced bone resorption were measured in the murine calvarial assay described in Example 1. Greater than 50% NDGA inhibition of bone resorption was noted for two different preparations of lipopolysaccharide. A summation of these results is seen in Table III.

TABLE III

Effects of NDGA on LPS Induced Bone Resorption in Murine Calvarial Assay

| LPS Used | Control | NDGA $10^{-5M}$ | LPS | LPS + NDGA | % Inhibition |
|---|---|---|---|---|---|
| AaY4 LPS 50 mg/ml | 15.4 ± 0.53 | 12.7 ± 0.8 | 31.3 ± 1.4 | 22.2 ± 2.8* | 57.2 |
| WR14 LPS 50 ng/ml | 12.8 ± 0.8 | 10.9 ± 0.5 | 35.2 ± 1.3 | 22.3 ± 2.3* | 57.6 |

Significant inhibition of the resorption effects of both bacterial lipopolysaccharide (LPS) preparations was observed with NDGA.

EXAMPLE 6

Effects of 5LO Inhibitor MK886 on Factor-induced Bone Resorption in the Murine Calvarial Assay The effects of 5LO inhibitor MK886 on bone resorption induced by 1,25 dihydroxyvitamin $D_3$ and bone resorption induced by Interleukin-1 were measured in the murine calvarial assay (as described in Example 1). The results of these measurements are shown in Table IV.

TABLE IV

Effects of MK886 on Factor Induced Bone Resorption in Murine Calvarial Assay

| Control | MK886 2.5 µg/ml | $1,25D_3$ $10^{-10}M$ | IL-1 $1 \times 10^{-10}M$ | | Inhibition |
|---|---|---|---|---|---|
| + | | | | 15.4 ± 0.6 | |
| | + | | | 9.6 ± 0.3 | |
| | | + | | 37.2 ± 0.7 | |
| | + | + | | 32.1 ± 2.4* | 23.4 |
| + | | | | 21.5 ± 1.6 | |
| | + | | | 14.2 ± 0.7 | |
| | | | + | 38.9 ± 2.4 | |
| | + | | + | 34.9 ± 1.7 | 23.0 |

As shown in Table IV, the 5LO inhibitor MK886 significantly inhibited 1,25 dihydroxyvitamin $D_3$-induced bone resorption. However, a significant inhibition of Interleukin-1 induced bone resorption was not noted.

EXAMPLE 7

Effects of NDGA and MK886 on Lipopolysaccharide-stimulated Resorption in the Murine Calvarial Assay The effects of NDGA and 5LO inhibitor MK886 were measured on lipopolysaccharide-stimulated bone resorption in the murine calvarial assay described in Example 1. Table V summarizes the results obtained with this study of bone resorption.

TABLE V

Effects of NDGA and MK886 in Combination on LPS Stimulated Resorption in the Murine Calvarial Assay

| C | MK886 | NDGA $10^{-5}$M | AAY4 LPS 25 μg/ml | WR14 LPS 50 ng/ml | $Ca^{45}$ Release | % Inhibition |
|---|---|---|---|---|---|---|
| + | | | | | 15.4 ± 1.4 | |
|   | | | + | | 24.5 ± 0.7 | |
|   | + | | + | | 22.6 ± 1.5 | 20.9 |
|   | | + | + | | 13.6 ± 0.4* | 119.8 |
|   | | | | + | 33.8 ± 1.1 | |
|   | + | | | + | 32.8 ± 1.8 | 8.2 |
|   | | + | | + | 26.3 ± 0.4* | 40.8 |

As shown in Table V, MK886 only mildly inhibited bone resorption induced by AaY4 LPS or WR14 LPS. With NDGA, LPS-induced resorption was significantly inhibited.

EXAMPLE 8

Effects of ZM 230,487 on PTH Induced Bone Resorption in the Murine Calvarial Assay (% Total Calcium Released)

The murine calvarial assay described in Example 1 was utilized to test the effects of the 5LO inhibitor ZM230487 on PTH-induced bone resorption. The results of this assay are seen in Table VI.

TABLE VI

Effects of ZM 230,487 on PTH Induced Bone Resorption in the Murine Calvarial Assay

| | | % Inhibition |
|---|---|---|
| Control | 12.1 ± 0.8 | |
| ZM 230,487 (100 ng/ml) | 11.1 ± 0.6 | |
| PTH (10 ng/ml) | 30.5 ± 2.4 | |
| PTH + 100 ng/ml ZM 230,487 | 17.7 ± 1.7* | 69.8 |
| PTH + 50 ng/ml ZM 230,487 | 23.3 ± 3.3* | 40.1 |

As shown in Table VI, a significant inhibition of bone resorption occurred at both concentrations of this 5LO inhibitor.

EXAMPLE 9

Effects of ZM 230,487 on Factor-Induced Bone Resorption Murine Calvarial Assay In the murine calvarial system of Example 1, the effects of the 5LO inhibitor ZM230487 was studied on bone resorption induced by Interleukin-1, tumor necrosis factor and lipopolysaccharide. The results are shown in Table VII.

TABLE VII

Effects of ZM 230,487 on Factor Induced Bone Resorption Murine Calvarial Assay

| Factor (Conc.) | Control | ZM 230,487 100 ng/ml | Factor | Factor + ZM 230,487 | % Inhibition |
|---|---|---|---|---|---|
| IL-10 $5 \times 10^{-10}$M | 15.2 ± 1.0 | 13.2 ± 0.4 | 32.0 ± 0.8 | 18.3 ± 0.4* | 81.7 |
| TNF $5 \times 10^{-10}$M | | | 27.7 ± 1.8 | 17.4 ± 0.5* | 82.4 |
| LPS WR14 50 ng/ml | 13.5 ± 0.4 | 12.6 ± 0.3 | 39.5 ± 1.1 | 18.5 ± 0.5 | 69.8 |

ZM 230,847, at 100 ng/ml; 25-fold less than MK886, 50-fold less than NDGA, as noted in other Examples) significantly inhibits bone resorption due to IL-1, TNF and LPS WR 14.

EXAMPLE 10

The Effects of NDGA, MK886 and ZM230487 on PTH and PTHrP-Induced Bone Resorption The effects of NDGA, MK886 and ZM230487 on PTH and PTHrP-induced bone resorption in the isolated fetal rat osteoclast assay described in Example 3 were measured. The results of these experiments are seen in FIGS. 12A–12D. It should be noted that inhibition of the bone resorption was seen with all three 5LO inhibitors, the order of inhibitory effectiveness, as noted in FIGS. 12A–12D, was ZM230487>MK886>NDGA.

EXAMPLE 11

Effect of the 5LO Inhibitor ZM230,487 on Rat Osteoclast Pit Formation

Figure 13A:
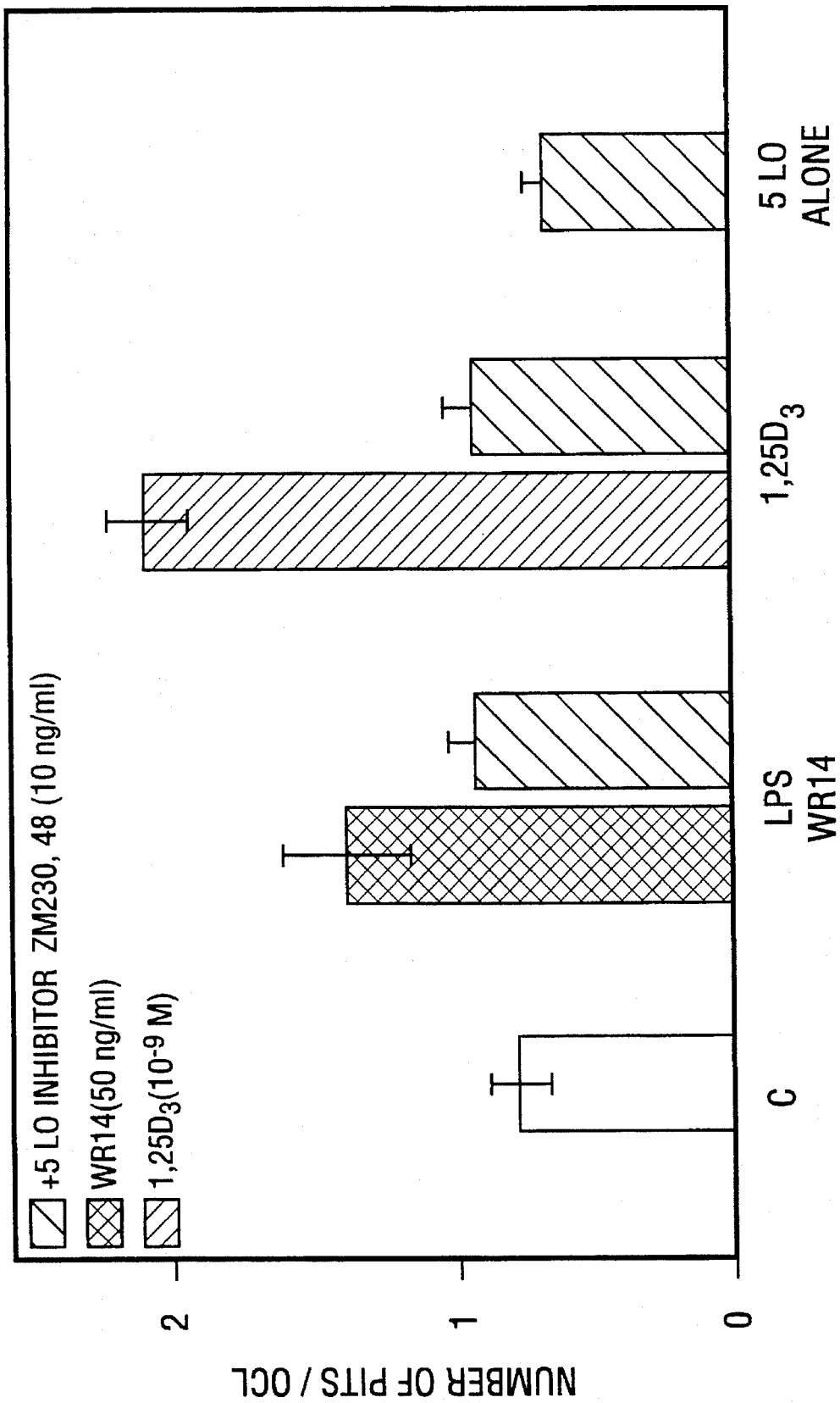
FIGS. 13A–13B show that ZM 230,487 significantly inhibits resorption due to 1,25(OH)$_2$ vitamin D$_3$. Significance was not reached in this experiment with WR14 LPS.
Figure 13B:
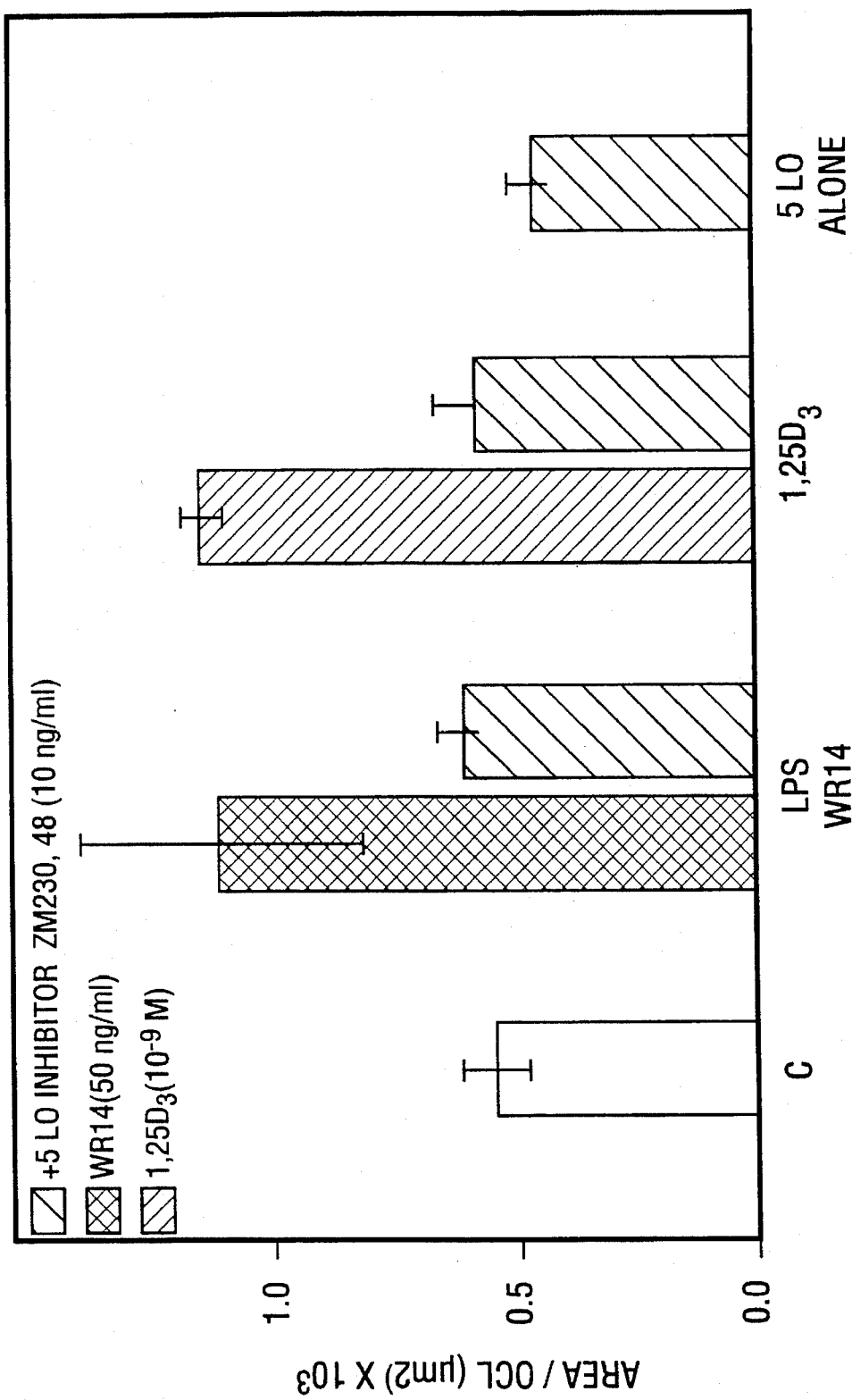

The rat osteoclast Assay of Example 3 was also used in the context of lipopolysaccharide-induced or 1,25-dihydroxyvitamin $D_3$-induced bone resorption. The results of these assays are seen in FIGS. 13A and 13B. It should be noted that the 5LO inhibitor ZM230487 effectively inhibited the induction of bone resorption by lipopolysaccharide, tumor necrosis factor, and 1,25 dihydroxyvitamin $D_3$.

The following citations are incorporated in pertinent fact by reference herein for the reasons cited in the above text.

REFERENCES

Agarwal et al., *Drug Metabolism and Disposition* 19:620, 1991.
Athanasou et al., *Br. J. Cancer*, 59:491–498, 1989.
Balazy et al., *Anal. Chem.*, 58:1098–1101, 1986.
Band et al., *J. Clin. Invest.*, 76:374–377, 1985.
Baud L. et al., *J. Clin. Invest.* 76: 374–377, 1985.
Boyde et al., *Br. Dent. J.*, 156:216–220, 1984.
Chambers et al., *J. Cell. Physiol.*, 132:90–96, 1987.
Chambers et al., *Calcif. Tissue Int.*, 35:566–570, 1983.
Chambers et al., *Endocrinology* 116:234, 1993.
Collin-Osdoby et al., *J. Bone Miner. Res.*, 6:1353–1365, 1991.
Collins et al., *J. Dent. Res.*, 66:1722, 1987.
Collins et al., *J. Dent. Res.*, 66:1771, 1987.
Davies et al., *J. Cell Biol.*, 109:1817–1826, 1989.
Dixon et al., *Nature*, 343:282–284, 1990.
El Attar et al., *J. Oral Pathol.*, 12:7–10, 1983.
Gallwitz et al., *J. Biol. Chem.* 368: 10087–10094, 1993.
Garrett et al., *J. Clin. Invest.*, 85:632–639, 1990.
Gillard et al., *Can. J. Physiol. Pharmacol.*, 67:456–464, 1989.
Goldman et al., *J. Immunol.*, 136:4631–4636, 1986.
Goldring et al., *Clin. Orthop. Rel. Res.*, 204:59–75, 1986.
Gowen et al., *Nature*, 306:378–380, 1983.
Horton et al., *Cancer Res.*, 45:5663–5669, 1985.
Huang et al., *J. Med. Chem.*, 32:1836–1842, 1989.
Huang et al., *J. Med. Chem.*, 33:1194–1200, 1990.
Kargman et al., *J. Biol. Chem.*, 264:13313–13320, 1989.
Khandwals et al., *Biochem. Pharmacol.*, 36:663–672, 1987.
Komiya et al., *Clin. Orthop. Relat. Res.*, 258:304–309, 1990.
Ling et al., *Arch. Pathol. Lab. Med.*, 112:65–69, 1988.
Lowry et al., *J. Biol. Chem.*, 193:265–275, 1951.
Maniatis et al., *Molecular Cloning: A Laboratory Manual*, 202–203, 1982.
Matsumoto et al., *Biochemistry*, 85:26–30, 1988.
McMillan et al., *Br J Pharmacol* 107:1042–1047, 1992.
McSheehy et al., *Endocrinology* 118: 824–828, 1986.
McSheehy et al., *Endocrinology*, 119:1654–1659, 1986.
McSheehy et al., *J. Immunol.*, 138:775–779, 1987.
Meghji et al., *Prostaglandins*, 36:139–149, 1988.
Mohammed et al., *Am. J. Orthod. Dentofacial Orthop.*, 95:231–237, 1989.
Mundy et al., *Bone and Mineral Research*, V:209–280, 1987.
Oreffo et al., *Clin. Orthop. Rel. Res.*, 1993.
Oreffo et al., *Endocrinology*, 126:3069–3075, 1990.
Oursler et al., *J. Bone Miner. Res.*, 6:375–385, 1991.
Parker, C. W., *Annu. Rev. Immunol.*, 5:65–84, 1987.
Perry et al., *Calcif. Tissue Int.*, 40:298–300, 1987.
Raftery et al., *Biol. Mass Spectrom.*, 21:509–516, 1992.
Raisz et al., *Advances in Bone and Mineral Research Annual*, II:286–310, 1984.
Reid et al., *J. Biol. Chem.*, 265:19818–19823, 1990.
Rodan et al., *Calcif. Tissue Int.*, 33:349–351, 1981.
Sandy et al., *Bone Miner.*, 5:155–168, 1989.
Smith, W. L., *Biochem. J.*, 259:315–324, 1989.
Van Inwegen et al., *J. Pharmacol. Exp. Ther.*, 241:117–124, 1987.
Zaidi et al., *Biochem. Biophys. Res. Commun.*, 159:68–71, 1988.
Zambonin-Zallone et al., *Anat. Embryol.*, 162:379–392, 1981.
Ziboh et al., *Cancer Res.*, 46:600–603, 1986.

What is claimed is:

1. A method for inhibiting bone resorption comprising administering 1-ethyl-6-[fluoro-5-(4-methoxy-3,4,5,6-tetrahydro-2H-pyran-4-yl)phenoxy]methyl-quinol-2-one to a subject in an amount suppressing production of an osteoclast-stimulating factor.

2. The method of claim 1 where the factor is a leukotriene, peptidoleukotriene, or 5-hydroxyeicosatetraenoic acid.

3. The method of claim 1 where the bone resorption is related to periodontal disease, osteoporosis, estrogen deficiency, Paget's disease, inflammatory bone loss, bone malignancy or hyperparathyroidism.

4. The method of claim 1 where the administering is enteral, parenteral or topical.

5. The method of claim 1 where the amount is from 0.1 to 10 mg/kg body weight/day.

6. A method for inhibiting bone resorption in a patient with periodontal disease, osteoporosis, estrogen deficiency, Paget's disease, inflammatory bone loss, bone malignancy or hyperparathyroidism, the method comprising administering 1-ethyl- 6-[fluoro-5-(4-methoxy-3,4,5,6-tetrahydro-2H-pyran-4-yl)phenoxy]methyl-quinol-2-one in an amount suppressing production of an osteoclast-stimulating factor.

7. The method of claim 6 where the factor is a leukotriene, peptidoleukotriene, or 5-hydroxyeicosatetraenoic acid.

8. The method of claim 6 where the administering is enteral, parenteral or topical.

9. The method of claim 6 where the amount is from 0.1 to 10 mg/kg body weight/day.

10. The method of claim 6 where a patient with periodontal disease is being treated and the administration is topical.

11. The method of claim 6 where a patient with osteoporosis is being treated and the administration is enteral.

* * * * *